United States Patent
Bar Yosef et al.

(10) Patent No.: US 9,561,207 B2
(45) Date of Patent: *Feb. 7, 2017

(54) LIPID COMPOSITIONS FOR THE TREATMENT OF GASTRO-INTESTINAL DISORDERS AND THE PROMOTION OF INTESTINAL DEVELOPMENT AND MATURATION

(71) Applicant: Enzymotec Ltd., Migdal Haemek (IL)

(72) Inventors: Fabiana Bar Yosef, Haifa (IL); Gai Ben Dror, Moshav Ofer (IL); Tzafra Cohen, Haifa (IL); Yael Lifshitz, Zicron Yacov (IL)

(73) Assignee: ENZYMOTEC LTD., Migdal Haemek (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,497

(22) Filed: Jul. 9, 2015

(65) Prior Publication Data

US 2016/0030377 A1 Feb. 4, 2016

Related U.S. Application Data

(63) Continuation of application No. 12/682,311, filed as application No. PCT/IL2008/001311 on Oct. 2, 2008, now Pat. No. 9,107,439.

(Continued)

(51) Int. Cl.
*A61K 31/201* (2006.01)
*A61K 31/20* (2006.01)
(Continued)

(52) U.S. Cl.
CPC ............. *A61K 31/231* (2013.01); *A21D 2/165* (2013.01); *A23D 7/001* (2013.01); *A23D 7/003* (2013.01);
(Continued)

(58) Field of Classification Search
CPC ........ A21D 2/165; A23D 7/001; A23D 7/003; A23K 1/164; A23K 1/1813; A23K 1/1846; A23L 1/296; A23L 1/3006; A23L 1/3008; A61K 31/23; A61K 31/231; A61K 31/232
See application file for complete search history.

(56) References Cited

U.S. PATENT DOCUMENTS 4,876,107 A  10/1989 King et al.
2003/0072865 A1  4/2003 Bindels et al.

FOREIGN PATENT DOCUMENTS

EP  0216419 A2  4/1987
EP  0 965 578 A1  12/1999
(Continued)

OTHER PUBLICATIONS

International Search Report issued Apr. 2, 2009 by the International Searching Authority (ISA/EPO) in connection with International Application No. PCT/IL2008/001311.
(Continued)

*Primary Examiner* — Savitha Rao
(74) *Attorney, Agent, or Firm* — John P. White; Cooper & Dunham LLP

(57) ABSTRACT

The present invention provides a use of a lipid composition for the preparation of a nutritional, pharmaceutical or nutraceutical composition or a functional food, for the prevention and treatment of gastrointestinal diseases and disorders, and for promoting intestinal development, maturation, adaptation and differentiation.

16 Claims, 4 Drawing Sheets

Related U.S. Application Data

(60) Provisional application No. 60/960,664, filed on Oct. 9, 2007.

(51) Int. Cl.
| | | |
|---|---|---|
| *A61P 1/00* | (2006.01) | |
| *A61P 1/04* | (2006.01) | |
| *A61P 29/00* | (2006.01) | |
| *A61K 31/231* | (2006.01) | |
| *A21D 2/16* | (2006.01) | |
| *A23D 7/00* | (2006.01) | |
| *A61K 31/23* | (2006.01) | |
| *A61K 31/232* | (2006.01) | |

(52) U.S. Cl.
CPC .............. *A23K 20/158* (2016.05); *A23K 50/10* (2016.05); *A23K 50/40* (2016.05); *A23L 33/115* (2016.08); *A23L 33/12* (2016.08); *A23L 33/40* (2016.08); *A61K 31/23* (2013.01); *A61K 31/232* (2013.01); *A23V 2002/00* (2013.01)

(56) References Cited

FOREIGN PATENT DOCUMENTS

| | | | |
|---|---|---|---|
| EP | 1034704 | A1 | 9/2000 |
| EP | WO 2007/088160 | A1 | 8/2007 |
| EP | 2143340 | A1 | 1/2010 |
| WO | WO 93/21912 | | 11/1993 |
| WO | WO 98/36745 | | 3/1998 |
| WO | WO 01/41581 | A1 | 6/2001 |
| WO | WO 2005/036987 | A1 | 4/2005 |
| WO | WO 2006/114791 | A1 | 11/2006 |
| WO | WO 2007/046699 | A2 | 4/2007 |
| WO | WO 2007/058523 | A1 | 5/2007 |
| WO | WO 2009/039101 | A1 | 3/2009 |

OTHER PUBLICATIONS

Written Opinion of the International Preliminary Examining Authority (IPEA/EPO) issued Sep. 15, 2009 in connection with International Application No. PCT/IL2008/001311.
International Preliminary Report on Patentability issued Oct. 20, 2009 by the International Preliminary Examining Authority (IPEA/EPO) in connection with International Application No. PCT/IL2008/001311.
"Betapol: A Breakthrough in Infant Formula Fats", World of Ingredients, C&S Publishers, vol. 3, pp. 41-42 (Jan. 1, 1996).
Koo et al., "Palm Olein in the Fat Blend of Infant Formulas: Effect on the Intestinal Absorption of Calcium and Fat, and Bone Mineralization", Journal of the American College of Nutrition, vol. 25, No. 2, pp. 117-122 (2006).
Artursson et al., "Correlation Between Oral Drug Absorption in Humans and Apparent Drug Permeability Coefficients in Human Intestinal Epithelial (CACO-2) Cells", Biochemical and Biophysical Research Communications, vol. 175, No. 3, pp. 880-885 (1991).
Shamir et al., "Intestinal and Systemic Effects of Oral Insulin Supplementation in Rats After Weaning", Digestive Diseases and Sciences, vol. 50, No. 7, pp. 1239-1244 (Jul. 2005).
Sukhotnik et al., "Dietary Palmitic Acid Modulates Intestinal Re-Growth After Massive Small Bowel Resection in a Rat", Pediatr Surg Int, 24:1313-1321 (2008).
Travadi et al., "Pentoxifyline Reduces the Incidence and Severity of Necrotizing Enterocolitis in a Neonatal Rat Model", Pediatric Research, vol. 60, No. 2, pp. 185-189 (2006).
Feng et al., "Heparin-Binding Epidermal Growth Factor-Like Growth Factor Promotes Enterocyte Migration and Proliferation in Neonatal Rats with Necrotizinf Enterocolitis", Journal of Pediatric Surgery, vol. 42, pp. 214-220 (2007).

Vicario et al., "Dietary Glutamine Affects Mucosal Functions in Fats with Mild DSS-Induced Colitis", The Journal of Nutrition, 137:1931-1937 (2007).
Camuesco et al., "Dietary Olive Oil Supplemented with Fish Oil, Rich in EPA and DHA (n-3) Polyunsaturated Fatty Acids, Attenuates Colonic Inflammation in Rats with DSS-Induced Colitis", The Journal of Nutrition, 135:687-694 (2005).
Kishimoto et al., "Rebamioide, an Antiulcer Drug, Prevents DSS-Induced Colitis Formulation in Rats", Digestive Diseases and Sciences, vol. 45, No. 8, pp. 1608-1616 (Aug. 2000).
Evans et al., "Dietary Supplementation With Orotate and Uracil Increases Adaptive Growth of Jejunal Mucosa After Massive Small Bowel Resection in Rats", Journal of Parenteral and Enteral Nutrition, vol. 29, No. 5, pp. 315-321 (2005).
Miller et al., "A Ballistic Bomb Calorimeter", Br. J. Nutr., vol. 13, pp. 501-508 (1959).
Murphy et al., "Energy Content of Stools in Normal Healthy Controls and Patients with Cystic Fibrosis", Archives of Disease in Childhood, vol. 66, pp. 495-500 (1991).
Lambert et al., "Prevention of Alterations in Intestinal Permeability is Involved in Zinc Inhibition of Acute Ethanol-Induced Liver Damage in Mice", The Journal of Pharmacology and Experimental Therapeutics, vol. 205, No. 3, pp. 880-886 (2003).
Ito et al., "Intestinal Microcirculatory Dysfunction During the Development of Experimental Necrotizing Enterocolitis", Pediatric Research, vol. 61, pp. 180-184 (Nov. 2, 2007).
Dvorak et al., "Epidermal Growth Factor Reduces the Development of Necrotizing Enterocolitis in a Neonatal Rat Model", Am. J. Physiol. Gastrointest. Liver Physiol., 282:G156-G164 (2002).
Kavanagh, "A breakthrough in infant formula fats", Oléaqineus, Corps Gras, Lipides, vol. 4, No. 3, pp. 165-168 (1997).
Hara et al., "Glycerol replacement corrects defective skin hydration, elasticity, and barrier function in aquaporin-3-deficient mice", PNAS, vol. 100, No. 12, pp. 7360-7365 (2003).
Lu et al., "Polyunsaturated Fatty Acid Supplementation Alters Proinflammatory Gene Expression and Reduces the Incidence of Necrotizing Enterocolitis in a Neonatal Rat Model", Pediatr Res. (2007), 61(4):427-432.
Souci et al., Food Composition and Nutrition Tables 7$^{th}$ Ed., Palm Oil, p. 207.
Souci et al., Food Composition and Nutrition Tables 7$^{th}$ Ed., Cocoa Butter, p. 198.
Lucas et al., "Randomised controlled trial of a synthetic triglyceride milk formula for preterm infants", Archives of Disease in Childhood (1997), 77:F178-F184.
Kavanuagh, "Betapol a Breakthrough in Infant Formula Fats", The World of Ingredients (1996), 41-42.
Gardner, Lipid Biotechnology (2002), p. 463.
Gruger et al, "Fatty Acid Composition of Fish Oils", U.S. Dept of the Interior, Fish and Wildlife Service, Bureau of Commercial Fisheries (1967), vol. 275, pp. 1-30.
Saify et al., "A Study on the Patty Acid Composition of Fish Liver Oil from Two Marine Fish, Eusphyra blochii and Carcharhinus bleekeri", Turk J Chem (2003), 27:251-258.
"Irritable Bowel Syndrome", http://web.archive.org/web/20131017152432/http://www.prevention.com/health-conditions/irritable-bowel-syndrome-ibs, downloaded from the internet on Jul. 21, 2014, dated Oct. 17, 2013.
Office Action issued Apr. 3, 2012 in connection with U.S. Appl. No. 12/682,311, filed Apr. 9, 2010.
Response to Office Action issued Apr. 3, 2012, filed Jun. 4, 2012, in connection with U.S. Appl. No. 12/682,311, filed Apr. 9, 2010.
Office Communication issued Aug. 2, 2012 in connection with U.S. Appl. No. 12/682,311, filed Apr. 9, 2010.
Response to Office Communication issued Aug. 2, 2012, filed Sep. 26, 2012, in connection with U.S. Appl. No. 12/682,311, filed Apr. 9, 2010.
Office Action issued Feb. 20, 2013 in connection with U.S. Appl. No. 12/682,311, filed Apr. 9, 2010.
Response to Office Action issued Feb. 20, 2013, filed May 20, 2013, in connection with U.S. Appl. No. 12/682,311, filed Apr. 9, 2010.
Office Action issued Jun. 18, 2013 in connection with U.S. Appl. No. 12/682,311, filed Apr. 9, 2010.

(56) References Cited

OTHER PUBLICATIONS

Response to Office Action issued Jun. 18, 2013, filed Dec. 18, 2013, in connection with U.S. Appl. No. 12/682,311, filed Apr. 9, 2010.
Final Office Action issued Mar. 18, 2014 in connection with U.S. Appl. No. 12/682,311, filed Apr. 9, 2010.
Response to Final Office Action issued Mar. 18, 2014, filed Aug. 18, 2014, in connection with U.S. Appl. No. 12/682,311, filed Apr. 9, 2010.
Notice of Allowance issued Jun. 1, 2015 in connection with U.S. Appl. No. 12/682,311, filed Apr. 9, 2010.
Office Action issued May 1, 2014 in connection with U.S. Appl. No. 14/136,373, filed Dec. 20, 2013.
Office Action issued Jul. 23, 2014 in connection with U.S. Appl. No. 14/136,373, filed Dec. 20, 2013.
Response to Office Action issued May 1, 2014, filed May 22, 2014, in connection with U.S. Appl. No. 14/136,373, filed Dec. 20, 2013.
Response to Office Action issued Jul. 23, 2014, filed Oct. 22, 2014, in connection with U.S. Appl. No. 14/136,373, filed Dec. 20, 2013.
Notice of Allowance issued Nov. 10, 2014 in connection with U.S. Appl. No. 14/136,373, filed Dec. 20, 2013.

LIPID COMPOSITIONS FOR THE TREATMENT OF GASTRO-INTESTINAL DISORDERS AND THE PROMOTION OF INTESTINAL DEVELOPMENT AND MATURATION

CLAIM OF PRIORITY

This application is a continuation of U.S. Ser. No. 12/682,311, filed Apr. 9, 2010, which is a §371 national stage of PCT International Application No. PCT/IL2008/001311, filed Oct. 2, 2008, which claims priority to U.S. Provisional Application No. 60/960,664, filed Oct. 9, 2007, the entire contents of each of which are hereby incorporated by reference in their entirety into this application.

FIELD OF THE INVENTION

This invention relates to the field of gastrointestinal diseases and disorders and intestinal development and maturation.

BACKGROUND OF THE INVENTION

Adequate neonatal nutrition is essential for appropriate growth and to avoid complications associated with nutritional deficiencies. Neonatal nutritional requirements vary with metabolic states, degree of prematurity and diseases affecting the gastrointestinal, pulmonary, and cardiac systems.

Infants may suffer from several digestive system disorders that may vary from light discomforts to sever life threatening diseases.

The rising incidence of preterm births, coupled with improved survival as a result of highly evolving technologies, has resulted in an increased need to develop innovative and cost-effective treatment modalities for preterm infants during the neonatal period and in later life. Pre-term babies do not achieve the intestinal maturity normally accreted during the third trimester of pregnancy, and are often born with immature gastrointestinal tract, and gastrointestinal diseases and disorders.

US2003/0072865 describes an infant formula comprising a lipid component in which palmitic acid residues make up more than 10% of total fatty acid residues present in the triglycerides resulting in reduced constipation, abdominal discomfort, and gastrointestinal problems.

Postnatal phases lead to maturation of intestinal epithelial cells occur in the early life of an animal: morphogenesis and cytodifferentiation prepare the epithelium for digestion and absorption of colostrums and milk components; thickening of occurs due to the growth of villi and crypts.

Epithelial structure and function of the gastrointestinal tract in neonates changes abruptly before weaning to adapt to a change in feeding from milk to solid food. Although intestinal maturation in the neonate has been the subject of intensive studies, the factors triggering the major biochemical and morphologic changes during maturation are still poorly understood. Newborn infants have a very immature cell lining in the intestines. The junctions between enterocytes are not tight, and the brush border and mucus layers are not fully developed. Due to the less tight mucosal barrier, the infant is at greater risk of contracting infections and developing allergies. Thus, intestinal maturation and differentiation of the gut barrier to protect against environmental aggression is desired During life, intestinal epithelial cells have to fulfill different roles, including classical digestive and absorptive functions, maintenance of a barrier against noxious antigens and bacteria, and secretion of water and electrolytes to keep a proper viscosity of the luminal contents and flush out oxious components.

Intestinal development, maturation, adaptation and ion are highly important in the course of a subject's life.

SUMMARY OF THE INVENTION

The present invention provides a use of a lipid composition comprising at least one triglyceride of the following formula I:

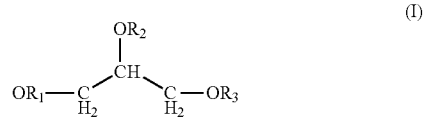

(I)

wherein $R_1$, $R_2$ and $R_3$ may be identical or different and are each independently selected from H or an acyl group, wherein said acyl group is selected from a group consisting of saturated, mono-unsaturated and poly-unsaturated fatty acid residues, and wherein the total palmitic acid residue content is from about 15% to about 55% of the total fatty acid residues in the composition, for the preparation of a nutritional, pharmaceutical or nutraceutical composition or a functional food, for the prevention and treatment of gastrointestinal diseases and disorders, and for promoting intestinal development, maturation, adaptation and differentiation.

The subject invention further envisages a method of treating a subject having, or having an increased risk of, gastrointestinal disease or disorder, and of promoting intestinal development, maturation, adaptation and differentiation comprising administering to the subject a lipid composition comprising at least one triglyceride of the following formula I:

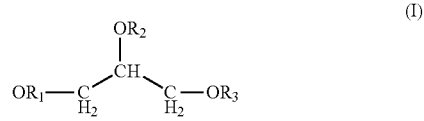

(I)

wherein $R_1$, $R_2$ and $R_3$ may be identical or different and are each independently selected from H or an acyl group, wherein said acyl group is selected from a group consisting of saturated, mono-unsaturated and poly-unsaturated fatty acid residues and wherein the total palmitic acid residue content is from about 15% to about 55% of the total fatty acid residues in the composition.

BRIEF DESCRIPTION OF THE DRAWINGS

In order to understand the invention and to see how it may be carried out in practice, embodiments will now be described, by way of non-limiting example only, with reference to the accompanying drawings in which.

§p<0.05 Diet A or Diet B vs Diet C
†p<0.05 Diet A vs Diet B

Figure 2:
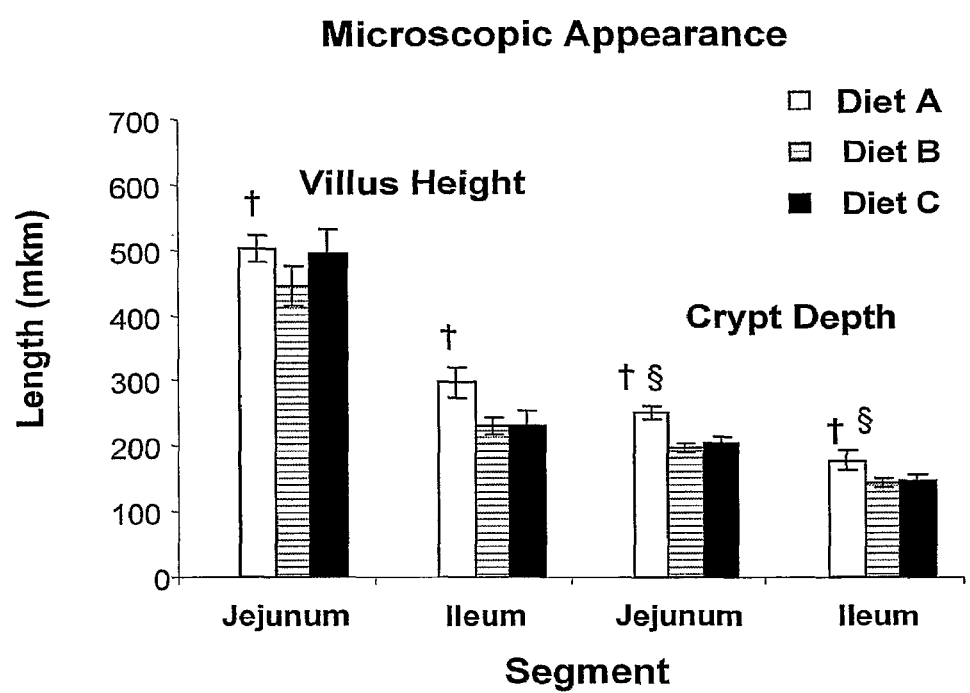

FIG. 2 demonstrates the effect of dietary treatment on microscopic bowel appearance of rats after 2 weeks of feeding. Values are mean±SEM. Diet A (containing oils enriched with a high content of palmitic acid at the sn-2 position), Diet B (containing a standard vegetable oil mixture with a high content of palmitic acid) and Diet C (containing oils with a low content of palmitic acid) were compared.

§p<0.05 Diet A or Diet B vs Diet C
†p<0.05 Diet A vs Diet B

Figure 3:
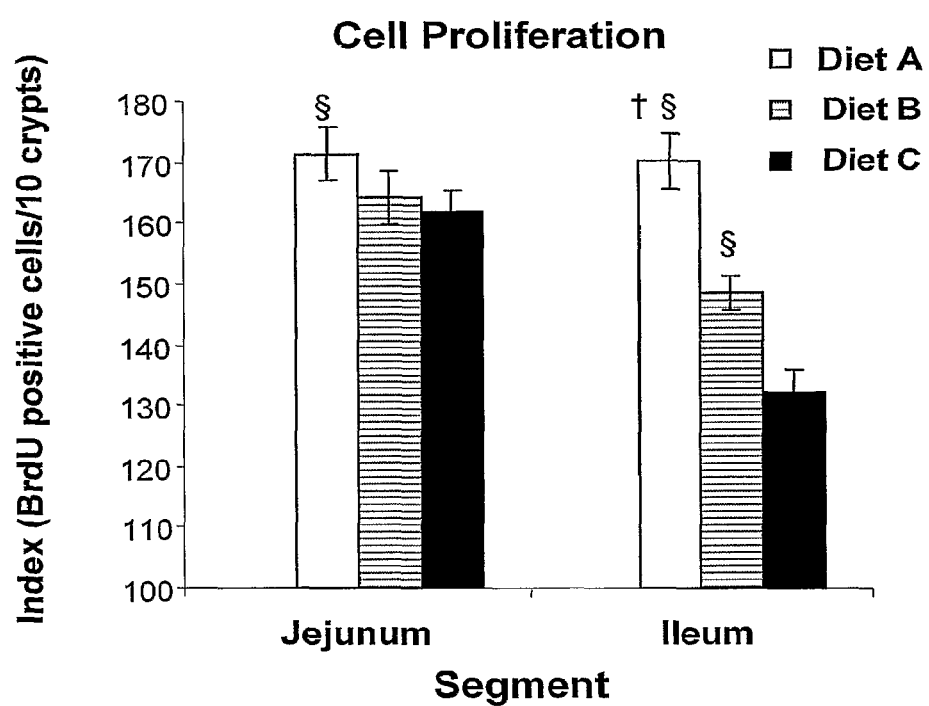

FIG. 3 demonstrates the effect of dietary treatment on enterocyte proliferation in rats after 2 weeks of feeding. 5-BrdU incorporation into proliferating jejunal and ileal crypt cells was detected with a goat anti-BrdU antibody. The number of labeled cells in 10 well-oriented, longitudinal crypts per section from each rat was determined using light microscopy. Values are mean±SEM. Diet A (containing oils enriched with a high content of palmitic acid at the sn-2 position), Diet B (containing a standard vegetable oil mixture with a high content of palmitic acid) and Diet C (containing oils with a low content of palmitic acid) were compared.

§p<0.05 Diet A or Diet B vs Diet C
†p<0.05 Diet A vs Diet B

Figure 4A:
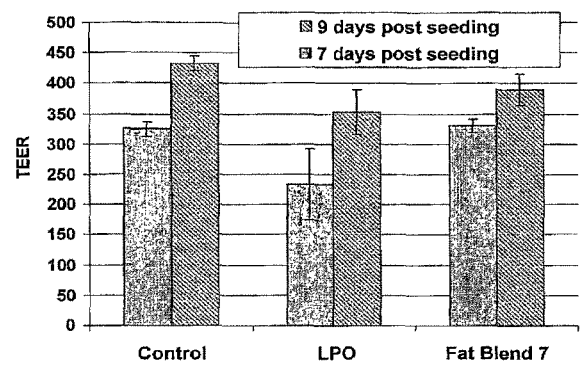
Figure 4B:
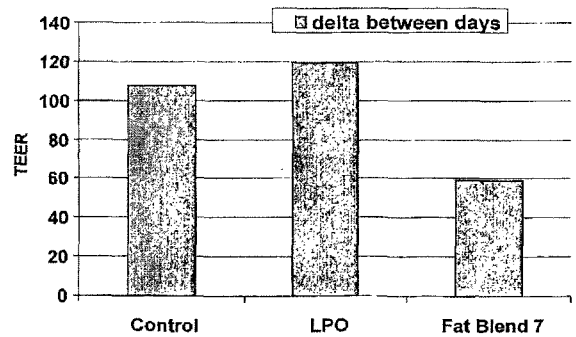

FIGS. 4A and 4B: Confluence and differentiation of the Caco-2 cells monolayer following incubation with Fat blend 7 (oil enriched with a high content of palmitic acid at the sn-2 position) in comparison to LPO (oil with a low content of palmate acid) were evaluated by Trans-Epithelial-Electrical-Resistance (TEER) measurements.

FIG. 4A depicts TEER values measurements of cells incubated for 7 and 9 days with 10 .mu.M of ilk-rent oils or control oil.

FIG. 4B depicts the delta in TEER values between day 7 and day 9 represent the additional increase in confluence and differentiation of the Caco-2 cells.

DETAILED DESCRIPTION OF THE INVENTION

The present invention provides a use of a lipid composition comprising at least one triglyceride of the following formula I:

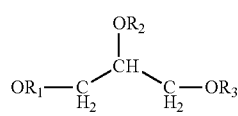

wherein $R_1$, $R_2$ and $R_3$ may be identical or different and are each independently selected from H or an acyl group, wherein said acyl group is selected from a group consisting of saturated, mono-unsaturated and poly-unsaturated fatty acid residues, and wherein the total palmitic acid residue content is from about 15% to about 55% of the total fatty acid residues in the composition, for the preparation of a nutritional, pharmaceutical or nutraceutical composition or a functional food, for the prevention and treatment of gastrointestinal diseases and disorders, and for promoting intestinal development, maturation, adaptation and differentiation.

The lipid composition used in the invention typically comprises a mixture of said triglycerides of formula I. Such a mixture comprises two or more triglycerides of formula I.

The present invention further envisages a method of treating a subject having, or having an increased risk of, gastrointestinal disease or disorder, and of promoting intestinal development, maturation, adaptation and differentiation comprising administering to the subject a lipid composition comprising at least one triglyceride of the following formula I:

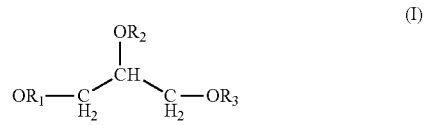

wherein $R_1$, $R_2$ and $R_3$ may be identical or different and are each independently selected from H or an acyl group, wherein said acyl group is selected from a group consisting of saturated, mono-unsaturated and poly-unsaturated fatty acid residues and wherein the total palmitic acid residue content is from about 15% to about 55% of the total fatty acid residues in the composition.

The present invention further envisages a method of preventing a gastrointestinal disease or disorder in a subject comprising administering to the subject a lipid composition comprising at least one triglyceride of the following formula I:

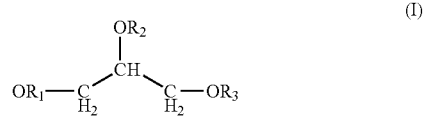

wherein $R_1$, $R_2$ and $R_3$ may be identical or different and are each independently selected from H or an acyl group, wherein said acyl group is selected from a group consisting of saturated, mono-unsaturated and poly-unsaturated fatty acid residues and wherein the total palmitic acid residue content is from about 15% to about 55% of the total fatty acid residues in the composition.

Compositions of the subject invention are intended for treating or preventing gastrointestinal diseases and disorders in a subject, and for promoting intestinal development, maturation, adaptation and differentiation.

The term "subject" as used herein should be understood to encompass any mammal, including, but not limited to, humans, household animals (e.g. cat, dog), and farm animals (e.g. cow, goat, ship). Said subject may be in any stage of development or maturity in its life cycle. The subject can be, but is not limited to, a newborn, a preterm and term infant, a toddler, a child, an adolescent, an adult or a geriatric subject.

An infant as used herein can be any infant, such as, but not limited to, a newborn, a preterm and term infant, small premature infants, which are susceptible to immature gastrointestinal tract, infants with very low birth weight (VLBW) or extreme low birth weight (ELBW), particularly those with increased risk of necrotizing enterocolitis and others.

A composition as used herein can be, but is not limited to, a nutritional composition (such as infant formula), a nutraceutical composition (such as a dietary supplement), a functional food, a medical food, or a pharmaceutical composition.

In one embodiment, a lipid composition for use in the invention is prepared from a natural, synthetic or semi-synthetic source. In a further specific embodiment, said natural source is any one of plant, animal or microorganism source. In yet a further embodiment, the production of said lipid composition involves an enzymatic catalysis.

A nutritional composition as used herein can be any nutritional composition including, but not limited to, human milk fat substitute, infant formula, dairy product, ice-cream, biscuit, soy product, bakery, pastry and bread, sauce, soup, prepared food, frozen food, condiment, confectionary, oils and fat, margarine, spread, filling, cereal, instant product, infant food, toddler food, bar, snack, candy and chocolate product.

A functional food as used herein can be any functional food, including, but not limited to, dairy product, ice-cream, biscuit, soy product, bakery, pastry and bread, sauce, soup, prepared food, frozen food, condiment, confectionary, oils and fat, margarine, spread, filling, cereal, instant product, drinks and shake, infant food, bar, snack, candy and chocolate product.

A nutraceutical composition as used herein can be any nutraceutical, which can be any substance that may be considered a food or part of a food and provides medical or health benefits, including the prevention and treatment of disease. Such nutraceutical compositions include, but are not limited to, a food additive, a food supplement, a dietary supplement, genetically engineered foods such as for example vegetables, herbal products, and processed foods such as cereals, soups and beverages and stimulant functional food, medical food and pharmafood.

In an embodiment of the invention, the pharmaceutical or nutraceutical compositions are in a dosage delivery form.

Suitable routes of administration for the compositions of the subject invention are oral, buccal and sublingual administration or administration via a feeding tube. In a specific embodiment, the compounds are administered orally.

The exact dose and regimen of administration of the composition will necessarily be dependent upon the therapeutic effect to be achieved (e.g. treatment of gastrointestinal disease) and may vary with the particular formula, the route of administration, and the ago and condition of the individual subject to whom the composition is to be administered.

The present invention thus also provides pharmaceutical compositions for use in the invention in admixture with pharmaceutically acceptable auxiliaries, and optionally other therapeutic agents. The auxiliaries must be "acceptable" in the sense of being compatible with the other ingredients of the composition and not deleterious to the recipients thereof.

In one embodiment, the pharmaceutical composition further comprises at least one pharmaceutically active agent.

The compositions may be prepared by any method well known in the art of pharmacy. Such methods include the step of bringing in association the ingredients with any auxiliary agent. The auxiliary agent(s), also named accessory ingredient(s), include those conventional in the art, such as carriers, fillers, binders, diluents, disintegrants, lubricants, colorants, flavouring agents, anti-oxidants, anti wetting agents.

Pharmaceutical compositions suitable for oral administration may be presented as discrete dosage units such as pills, tablets, dragées or capsules, or as a powder or granules, or as a solution or suspension.

The compositions may be presented in unit-dose or multi-dose containers, for example sealed vials and ampoules, and may be stored in a freeze-dried (lyophilised) condition requiring only the addition of sterile liquid carrier, for example water, prior to use.

The invention further provides a commercial package for preparing a composition for use in the invention such as an edible fat source or food article in accordance with the invention comprising (a) a fat source which upon enteral administration to a subject prevents or treats digestive system disorders, and/or promotes intestinal development, maturation, adaptation and differentiation; (b) optionally at least one of edible physiologically acceptable protein, carbohydrate, vitamin, mineral, amino acid, nucleotide and active or non-active additive; (c) optionally at least one edible physiologically acceptable carrier or diluent for carrying the constituent/s defined in (a) and (b); (d) means and receptacles for admixing the constituents defined in (a), (b) and/or (c); and (e) instructions for use such as, but not limited to terms of storage, instructions for preparation of the fat source or food article for administration, required dilutions, dosages, frequency of administration and the like.

A commercial package in accordance with the invention may also contain a fat source of the invention in a ready-to-use form, together with instructions for use. Dosages are usually determined according to age, weight, sex and condition of the subject, in accordance with good medical practice known to the attending physician and other medical personnel.

Gastrointestinal disease or disorder as used herein should be understood to encompass gastroesophageal reflux (GER), Gastroesophageal reflux disease (GERD), necrotizing enterocolitis (NEC), Hyperbillirubinemia, Inflammatory bowel diseases (such as but not limited to Crohn's disease and Ulcerative colitis), short bowel syndrome, intestinal sections or incisions, intestinal re-anastomosis, ulcer, surgical interventions for example for treating intestinal adhesions, and intestinal obstruction.

The term "intestine" as used herein should be understood to encompass a segment of the alimentary canal extending from the stomach to the anus. In humans and other mammals, the intestine consists of two segments, the small intestine (in humans further subdivided into the duodenum, jejunum and ileum) and the large intestine (in humans further subdivided into the cecum and colon). Other mammals may have a further complexed intestine.

Promoting intestinal development as used herein should be understood to encompass promoting a process or part of a process of enhancing, increasing, growing, supporting or advancing the formation of a specialized mature epithelium.

Promoting intestinal maturation as used herein should be understood to encompass promoting a process or part of a process of enhancing, increasing, growing, supporting or advancing the differentiation processes of enterocyte and intestinal segments.

Both intestinal (segment) development and maturation may be measured by intestinal mucosal parameters such as, but not limited to bowel circumference, bowel weight and mucosal weight and by histological changes such as but not limited to villus height and crypt depth.

Promoting intestinal adaptation as used herein should be understood to encompass any physiological change by which the absorptive capacity of the small intestine is enhanced, increased, grown, supported or advanced including, but not limited to, enlargement or lengthening of the villi found in the lining, increase in the diameter of the small intestine and slow down in peristalsis or movement of food through the small intestine.

Promoting intestinal differentiation as used herein should be understood to encompass a process by which a pre-differentiated cell becomes a specialized cell type. For example, in case of intestinal differentiation, pluripotent stem cells, localized near the base of the crypt, are fitly differentiated into one of the four primary cell types: absorptive enterocytes, goblet cells, Paneth cells, and enteroendocrine cells.

GER (Gastroesophageal reflux) is a disorder wherein the liquid gastric contents are squirted backwards. Instead of squirting down into the intestines, they squirt up into the esophagus. In infants the major cause of GER is immaturity of lower esophageal sphincter. When the reflux damages the esophagus it is called GERD.

GERD (Gastroesophageal reflux disease) is a disorder with chronic symptoms or mucosal damage produced by the abnormal reflux in the esophagi's. This is commonly due to transient or permanent changes in the barrier between the esophagus and the stomach GERD is more evident in babies having pre mature or a not fully developed gastro intestinal tract.

Hyperbillirubinemia is common and in most cases a benign problem. The color usually results from the accumulation in skin of unconjugated, non-polar, lipid-soluble billirubin pigment. The toxic effect of elevated levels of unconjugated billirubin in serum is increased by several factors, such as free fatty acids, that reduce the retention of billirubin in the circulation.

NEC is a gastrointestinal disease that mostly affects premature infants; it involves infection and inflammation that causes destruction of the bowel (intestine) or part of the bowel. NEC is the most common and serious gastrointestinal disorder among hospitalized preterm infants.

Studies have shown that the risk of NEC is increased as the infant is born earlier and that the risk of breast fed infants is lower than infants that are formula-fed.

NEC typically occurs after milk feeding has begun. Premature infants have immature bowels, which are sensitive to changes in blood flow and prone to infection.

The exact cause of NEC is unknown, but several theories exist. It is thought that the intestinal tissues of premature infants are weakened by too little oxygen or blood flow, and when feedings are started, the added stress of food moving through the intestine allows bacteria that are normally found in the intestine to invade and damage the wall of the intestinal tissues.

The infant is unable to continue feedings and starts to appear ill if bacteria continue to spread through the wall of the intestines and sometimes into the bloodstream. Because the infant's body systems are immature, even with quick treatment for NEC there may be serious complications.

Other factors seem to increase the risk of developing NEC. Some experts believe that the makeup of infant formula, the rate of delivery of the formula, or the immaturity of the mucous membranes in the intestines can cause NEC.

Inflammatory bowel disease (IBD) is a group of inflammatory conditions of the large intestine and small intestine. The major types of IBD are Crohn's disease and ulcerative colitis. Ulcerative colitis is an inflammatory disease of the large intestine. In ulcerative colitis, the inner lining—or mucosa—of the intestine becomes inflamed (meaning the lining of the intestinal wall reddens and swells) and develops ulcers meaning an open, painful wound. Inflammatory bowel disease (IBD) may cause symptoms such as, but not limited to, bloody stools, occult blood in the stool, body weight loss, bloody diarrhea, reduced physical activity, severe anemia, shortened colonic length, and perianal injury. Crohn's disease differs from ulcerative colitis in the areas of the bowel it involves—it most commonly affects the last part of the small intestine (called the terminal ileum) and parts of the large intestine. However, Crohn's disease isn't limited to these areas and can attack any part of the digestive tract Crohn's disease causes inflammation that extends much deeper into the layers of the intestinal wall than ulcerative colitis does. Crohn's disease generally tends to involve the entire bowel wall, whereas ulcerative colitis affects only the lining of the bowel.

Short bowel syndrome (SBS) is a malabsorption disorder caused by the surgical removal of the small intestine, or rarely due to the complete dysfunction of a large segment of bowel. Most cases are acquired, although some children are born with a congenital short bowel. SBS usually does not develop unless a person has lost more than two thirds of their small intestine.

Surgical intervention as used herein should be understood to encompass an intervention for e.g. diagnosis and/or treatment of injury, deformity, or disease. Such intervention may involve an operation or procedure in the gastrointestinal tract, such as, but not limited to, an intestinal section or incision and intestinal reanastomosis. Such an intestinal section or incision may be a cut or a wound made by cutting the intestine with a sharp instrument, such as one used during surgery.

Intestinal reanastomosis is a connection between two vessels in the body. Surgical anastomosis involves the deliberate joining of two vessels or hollow parts of an organ; for example, when part of the intestine has been removed and the remaining free ends are brought together and stitched.

Intestinal adhesions are bands of fibrous tissue that can conned the loops of the intestines to each other, or the intestines to other abdominal organs, or the intestines to the abdominal wall. These bands can pull sections of the intestines out of place and may block passage of food. Adhesions are a major cause of intestinal obstruction. Adhesions may be present at birth (congenital) or may form after abdominal surgery or inflammation.

Intestinal obstruction refers to the partial or complete mechanical or nonmechanical blockage of the small or large intestine. Infants under one year of age are most likely to have intestinal obstruction caused by *meconium ileus*, volvulus, and intussusception. *Meconium ileus*, which is the inability to pass the fast fecal excretion after birth (*meconium*), is a disorder of newborns. It may also occur in very low birth weight (VLBW) infants, In *meconium ileus*, the abnormal *meconium* must be removed with an enema or through surgery. Volvulus is twisting a either the small or large bowel, that may cut off the blood supply to the bowel, leading to tissue death (gangrene). In intussusception, the bowel telescopes into itself like a radio antenna folding up. It is most common in children between the ages of three and nine months, although it also occurs in older children. Almost twice as many boys suffer intussusception as girls.

A fat source is used in the preparation of a composition (such as an infant formula) for use in the subject invention. Such composition, for example an infant formula, may further comprise other components such as, but not limited to a protein source, a carbohydrate source, minerals, vitamins, nucleotides, amino acids and optionally at least one of a carrier, diluent, additive or excipient, all of which are edible.

A fat blend as used herein for the preparation of a composition for use in the invention, such as an infant formula, can be, but is not limited to, any fat source, such as those described in WO05/036987, which include fat concentrates (also named fat bases). The fat blend used in the present invention can be any dietary ingredient comprising an edible fat source. In a particular embodiment, fat blends are those which are based on synthetic triglycerides (which can be produced both chemically and enzymatically) which mimic the triglyceride composition of human breast milk fat. In one embodiment, such fat base (and fat blend) contains a high level of palmitic acid at the sn-2 position of the triglycerides of formula I (e.g., at least 30%), and a high level of unsaturated fatty acids at sn-1 and sn-3 positions of the triglyceride of formula I (e.g. at least 50% of the total fatty acid at sn-1 and sn-3 positions). A non-limiting example is a blend named InFat® (Enzymotec Ltd., Migdal HaEmeq, Israel).

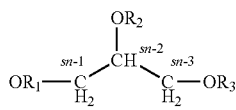

(I)

Since fat blends are prepared by blending fat base with other oils, the fatty acid composition of the fat blends results from the fatty acid composition of both the fat base and the other oils mixed with the fat base.

Infant formula used in the subject invention can be a substitute human milk fat composition comprising a fat blend consisting of at least 25% of a fat base with up to 75% of at least one vegetable oil.

Non-limiting examples of vegetable oil used in the preparation of blends used in the invention are soy, palm tree, canola, coconut, palm kernel, sunflower, corn and rapeseed oil, as well as other vegetable oils and fats and mixtures thereof.

As used herein, the term "lipid" related to fats and fatlike compounds, which are essentially insoluble in water and which include, but are not limited to, triglycerides, sterols, fatty acids, and so forth.

As used herein, the term "acyl group" relates to an organic radical denoted —C(=O)R, wherein R is selected from saturated, mono-unsaturated and polyunsaturated $C_4$-$C_{28}$ aliphatic residue of the fatty acid residue.

As used herein, the term "fatty acid" relates to a carboxylic acid with a long unbranched aliphatic tail (chain), which is either saturated or unsaturated having one unsaturated bond (mono-unsaturated fatty acids) or two or more unsaturated bonds (poly-unsaturated fatty acids).

Non-limiting examples of saturated fatty acids which may be used in this invention include: Butyric acid (Butanoic acid, C4:0), Caproic acid (Hexanoic acid, C6:0), Caprylic acid (Octanoic acid, C8:0), Capric acid (Decanoic acid, C10:0), Laurie acid (Dodecanoic acid, C12:0), Myristic acid (Tetradecanoic acid, C14:0), Palmitic acid (Hexadecanoic acid, C16:0), Stearic acid (Octadecanoic acid, C18:0), Arachidic acid (Eicosanoic acid, C20:0), Behenic acid (Docosanoic acid C22:0).

Non-limiting examples of unsaturated fatty acids which may be used in this invention include: Myristoleic acid (ω-5, C14:1), Palmitoleic acid (ω-7, C16:1), Oleic acid (ω-9, C18:1), Linoleic acid (ω-6, C18:2), Alpha-linolenic acid (ω-3, C18:3), Arachidonic acid (ω-6, C20:4), Eicosapentaenoic acid (ω-3, C20:5), Erucic acid (ω-9, C22:1) and Docosahexaenoic acid (ω-3, C22:6).

In one embodiment of the invention, $R_2$ is a saturated fatty acid residue. In a further embodiment, the saturated fatty acid residue is selected from $C_{14}$-$C_{18}$ saturated fatty acid residues. In yet a further embodiment, the saturated fatty acid is a palmitic acid residue.

In one embodiment, the total palmitic acid residue content is from about 15% to about 40% of the total fatty acid residues in the composition. In another embodiment, the total palmitic acid residue content is from about 15% to about 33% of the total fatty acid residues in the composition.

In another embodiment of the invention, $R_1$ and $R_3$ are both H.

In one embodiment, at least 13% of the total fatty acids at the sn-2 position of the triglyceride backbone are palmitic acid residues. In another embodiment, at least 15% of the total fatty acids at the sn-2 position of the triglyceride backbone are palmitic acid residues. In yet another embodiment, at least 18% of the total fatty acids at the sn-2 position of the triglyceride backbone are palmitic acid residues. In yet another embodiment, at least 22% of the total fatty acids at the sn-2 position of the triglyceride backbone are palmitic acid residues.

In one embodiment, at least 30% of the total palmitic acid residues in the composition are bonded at the sn-2 position of the triglyceride backbone. In another embodiment, at least 33% of the total palmitic acid residues are bonded at the sn-2 position of the triglyceride backbone. In yet another embodiment, at least 38% of the total palmitic acid residues are bonded at the sn-2 position of the triglyceride backbone. In yet another embodiment, at least 40% of the total palmitic acid residues are bonded at the sn-2 position of the triglyceride backbone.

In a further embodiment of the invention, $R_1$ and $R_3$ are unsaturated fatty acid residues.

In one embodiment, at least 50% of the total fatty acid residues at the sn-1 and sn-3 positions of the triglyceride backbone are unsaturated. In a further embodiment, at least 70% of the total fatty acid residues at the sn-1 and sn-3 positions of the triglyceride backbone are unsaturated. In one embodiment, said unsaturated fatty acid residue is selected from the group consisting of oleic acid, linoleic acid, linolenic acid and gadoleic acid. In one specific embodiment, at least 35% of the unsaturated fatty acid residues at the sn-1 and sn-3 positions are oleic acid residues. In a further specific embodiment, at least 40% of the unsaturated fatty acid residues at the sn-1 and sn-3 positions are oleic acid residues.

La one specific embodiment, at least 4% of said unsaturated fatty acid residues at the sn-1 and sn-3 positions are linoleic acid residues. In a further specific embodiment, at least 6% of said unsaturated fatty acid residues at the sn-1 and sn-3 positions are linoleic acid residues.

In a first embodiment, said lipid composition consists of:
0-10% C8:0 fatty acids out of the total fatty acids;
0-10% C10:0 fatty acids out of the total fatty acids;
0-22% C12:0 fatty acids out of the total fatty acids;
0-15% C14:0 fatty acids out of the total fatty acids;
15-55% C16:0 fatty acids out of the total fatty acids;
  wherein at least 30% at sn-2 position;
1-7% C18:0 fatty acids out of the total fatty acids;
20-75% C18:1 fatty acids out of the anal fatty acids;
2-40% C18:2 fatty acids out of the total fatty acids;

0-8% C18:3 fatty acids out of the total fatty acids;
other fatty acids are present in levels of less than 8% of the total fatty acids.

In a second embodiment, said lipid composition consists of:
5-15% C12:0 fatty acids out of the total fatty acids;
2-10% C14:0 fatty acids out of the total fatty acids;
17-25% C16:0 fatty acids out of the total fatty acids; wherein at least 40% at sn-2 position;
2-5% C18:0 fatty acids out of the total fatty acids;
28-45% C18:1 fatty acids out of the total fatty acids;
5-20% C18:2 fatty acids out of the total fatty acids;
1-3% C18:3 fatty acids out of the total fatty acids;
other fatty acids are present in levels of less than 5% of the total fatty acids.

All possible combinations of said first and said second embodiments e also envisaged.

For example:
0-22% C12:0 fatty acids out of the total fatty acids, (from the first embodiment) can be combined with
2-10% C14:0 fatty acids out of the total fatty acids;
20-25% C16:0 fatty acids out of the total fatty acids;
2-5% C18:0 fatty acids out of the total fatty acids;
28-45% C18:1 fatty acids out of the total fatty acids;
5-20% C18:2 fatty acids out of the total fatty acids;
1-3% C18:3 fatty acids out of the total fatty acids; other fatty acids are present in levels of less than 5% of the total fatty acids.

It is to be understood that the compounds provided herein may contain chiral centers. Such chiral centers may be of either the (R) or (S) configuration, or may be any mixture thereof. Thus, the compounds provided herein may be enantiomerically pure, or be stereoisomeric or diastereomeric mixtures such as racemic or non-racemic mixtures.

EXAMPLES

The invention is further described in the following examples, which are not in any way intended to limit the scope of the inventions as claimed.

Example 1

Compositions

Table 1 details the contents of several fat bases enriched with a high content of palmitic acid at the sn-2 position (hereinafter "fat bases"). Table 2 details the contents of several fat sources (hereinafter "fat blends") comprising either fat base 1, 7, 8, 9, 10 or 11 for use in the subject invention.

The fat base may represent about 30% up to about 83% of the fat blends suitable for use in a formula for use in the invention.

The preparation of these fat sources is essentially as described in WO05/036987.

TABLE 1

| | fat base 1 | fat base 2 | fat base 3 | fat base 4 | fat base 5 | fat base 6 | fat base 7 | fat base 8 | fat base 9 | fat base 10 | fat base 11 |
|---|---|---|---|---|---|---|---|---|---|---|---|
| C12:0 | | | | | | | | | | | |
| C14:0 | | | | | | | | | | | |
| C16:0 | 32 | 29.4 | 29.6 | 32.6 | 32.2 | 30.6 | 29 | 29 | 30 | 33 | 30 |
| C16:0 at sn-2 of total fatty acids at sn-2 | 67.2 | 59.7 | 61.3 | 66.1 | 66 | 62.9 | 53.9 | 55.6 | 59 | 52.9 | 55.8 |
| Ratio (%) of sn-2 palmitic acid of total palmitic acid | 70.0 | 67.7 | 69.0 | 67.6 | 68.3 | 68.5 | 62 | 64 | 64 | 53.5 | 62 |
| C18:0 | 4 | 4.4 | 4.4 | 4 | 4.1 | 3.8 | 2.6 | 2.6 | 3 | 3 | 3 |
| C18:1 | 53.1 | 55.9 | 55.5 | 53.1 | 53.4 | 55 | 55.5 | 56 | 56.1 | 52 | 56.1 |
| C18:2 | 8 | 7.8 | 8.2 | 8 | 7.9 | 8.3 | 9 | 9 | 8.5 | 10 | 8.5 |

All numbers represent % (w/w), except the ratio which is defined as %.
C16:0 represents the total palmitic acid content.
C16:0 at the sn-2 represents the % palmitic acid at sn-2 of total sn-2 positioned fatty acids.
The ratio means the % of sn-2 palmitic acid of total palmitic acid {(% of sn-2 palmitic of total sn-2 positioned fatty acids)/3)/(% total palmitic acid)} × 100.

TABLE 2

| | Preparation A Fat blend 1 | Preparation B Fat blend 2 | Preparation C Fat blend 3 | Preparation D Fat blend 4 | Preparation E Fat blend 5 | Preparation F Fat blend 6 | Preparation G Fat blend 7 | Preparation H Fat blend 8 | Preparation I Fat blend 9 | Preparation J Fat blend 10 |
|---|---|---|---|---|---|---|---|---|---|---|
| Fatty acid | | | | | | | | | | |
| C12:0 | 11.1 | 7.2 | 7.8 | 6.5 | 4.4 | 8.1 | 8.7 | 13.4 | 10.1 | 10 |
| C14:0 | 4.5 | 3.1 | 3.3 | 2.8 | 2.1 | 2.9 | 3.5 | 5.3 | 3.7 | 4.2 |
| C16:0 | 22.8 | 25.4 | 26.9 | 25.1 | 27.7 | 21.6 | 21 | 15 | 22.1 | 17 |
| C16:0 at sn-2 of total fatty acids at sn-2 | 33.4 | 42.9 | 48.9 | 50.8 | 56.9 | 31.3 | 31.8 | 25 | 28.7 | 16 |
| Ratio (%) of sn-2 palmitic acid of total palmitic acid | 48.7 | 56.3 | 60.7 | 67.4 | 68.5 | 48.3 | 50.5 | 55 | 43.3 | 31.5 |
| C18:0 | 2.3 | 3.0 | 3.1 | 3.5 | 4.0 | 2.6 | 2.6 | 2.9 | 2.7 | 3.2 |
| C18:1 | 38.4 | 40.8 | 41.6 | 47.9 | 46.6 | 42.7 | 44.4 | 39.7 | 43.9 | 41.7 |

TABLE 2-continued

| | Preparation A Fat blend 1 | Preparation B Fat blend 2 | Preparation C Fat blend 3 | Preparation D Fat blend 4 | Preparation E Fat blend 5 | Preparation F Fat blend 6 | Preparation G Fat blend 7 | Preparation H Fat blend 8 | Preparation I Fat blend 9 | Preparation J Fat blend 10 |
|---|---|---|---|---|---|---|---|---|---|---|
| C18:2 | 13.5 | 15.6 | 12.8 | 8.6 | 11.7 | 18 | 16.4 | 15.3 | 13.6 | 18.2 |
| C18:3 | 1.7 | 0.6 | | 1.4 | | 1.8 | 1.5 | 2 | 1.4 | 2.1 |
| % Fat base 1 in fat blend | 30 | 50 | 63 | 73 | 83 | | | | | |
| % Fat base 7 in fat blend | | | | | | 60 | | | | |
| % Fat base 8 in fat blend | | | | | | | 60 | | | |
| % Fat base 9 in fat blend | | | | | | | | 36 | | |
| % Fat base 10 in fat blend | | | | | | | | | 52 | |
| % Fat base 11 in fat blend | | | | | | | | | | 25 |
| Vegetable Oil | | | | | | | | | | |
| Palm kernel Oil | | | | | | 18 | | | | |
| Coconut oil | 23 | 15 | 16 | 13.5 | 9.3 | | 17 | 28 | 21 | 21 |
| Palm oil | 21 | 15 | 9 | | | | | | | 14 |
| Sunflower | | 5 | | | 7.7 | | | 11 | | 14 |
| Corn oil | 10 | 10 | 12 | | | | | | 11 | |
| Safflower | | | | | | | | 3 | | 5 |
| Rapeseed | 16 | 5 | | 13.5 | | 4 | 6 | 20 | 16 | 11 |
| Soybean | | | | | | 18 | 17 | | | |
| Total | 100 | 100 | 100 | 100 | 100 | 100 | 100 | 100 | 100 | 100 |

C16:0 represents the total palmitic acid content.
C16:0 at the sn-2 represents the % palmitic acid at sn-2 of total sn-2 positioned fatty acids.
The ratio means the % of sn-2 palmitic acid of total palmitic acid (% of sn-2 palmitic of total sn-2 positioned fatty acids)/3)/(% total palmitic acid)} × 100. All numbers represent % (w/w), except the ratio which is defined as %.

Example 2

Infant Formula

An infant formula comprising a fat base and additional oils and fats (i.e. fat blends) that mimic the human breast milk fat composition were prepared as follows:

The fat fraction was produced by blending of fat base with other ed together with other infant formula components (proteins, carbohydrates, minerals, vitamins and others). The slurry was passed through a pressure homogenizer to get a stable emulsion. Homogenized product was then dried in a spray drier to obtain final product Other additives may be added to the dry powder to obtain final formulation.

The fat fraction produced by the blending of fat base with other oils and fats as described above was further blended with other nutrients such as proteins, minerals, vitamins and carbohydrates to yield a food product supplying an infant with the major nutrients also found in human milk. The nutrients and fats were homogenized using pressure homogenization and spray dried to yield a homogenous powder. The powder was further re-dispersed in water (approx. 9 g powder per 60 ml water) to yield a ready-to-feed formula. The fat content of the ready feed was approx. 3.5 g per 100 ml which corresponds to the fat content of human breast milk, which is in the range of 30-40 g/L.

Table 3 shows the fatty acid composition of Fat bleed g a fat base of the invention (30%) which is mixed/blended with other oils and fats used to create a fat source used in an infant formula for use in the invention. Table 4 shows details of the ingredients and properties of the infant formula comprising the fat source of Table 3. Since fat blends are prepared by blending fat base with other oils, the fatty acids composition of the blends results from the fatty acids composition of both the fat base and of the other oils mixed with the fat base.

TABLE 3

| Fatty acid | % of fatty acids |
|---|---|
| C10:0 | 1.3 |
| C12:0 | 10.3 |
| C14:0 | 4.3 |
| C16:0 | 23.5 |
| C16:0 at sn-2 of total fatty acids at sn-2 | 30.3 |
| Ratio (%) of sn-2 palmitic acid of total palmitic acid | 43 |
| C18:0 | 3.2 |
| C18:1 | 39.2 |
| C18:2 | 13.6 |
| C18:3 | 1.7 |
| C20:0 | 0.3 |
| C20:1 | 0.3 |
| C22:0 | 0.2 |

All numbers represent % (w/w), except the ratio which is defined as %. C16:0 represents the total palmitic acid content. C16:0 at the sn-2 represents the % palmitic acid at sn-2 of total sn-2 positioned fatty acids. The ratio means the % of so-2 palmitic acid of total palmitic acid {(% of sn-2 palmitic of total sn-2 positioned fatty acids)/3)/(% total palmitic acid)}×100.

TABLE 4

| Formula | Per 100 g powder | Per 100 ml ready to feed |
|---|---|---|
| Energy (kcal) | 508 | 68 |
| Sodium (mg) | 140 | 18.8 |
| Protein (g) (Lacatalbumin/Casein 60/40) | 11.4 | 1.5 |
| Fat (gr) | 26.5 | 3.5 |
| Saturated fat (gr) | 11.3 | 1.49 |
| Linoleic acid (mg) | 5000 | 670 |
| Alpha-linolenic acid (mg) | 530 | 71 |
| Arachidonic acid (mg) | 115 | 15.3 |

TABLE 4-continued

| Formula | Per 100 g powder | Per 100 ml ready to feed |
|---|---|---|
| Docosahexaenoic acid (mg) | 108 | 14.4 |
| Cholesterol (mg) | 2 | 0.3 |
| Lactose (gr) | 56 | 7.5 |
| Calcium (mg) | 430 | 57.3 |
| Phosphorus (mg) | 250 | 33.5 |
| Potassium (mg) | 420 | 56.3 |
| Chloride (mg) | 300 | 40.2 |
| Iron (mg) | 5.25 | 0.7 |
| Magnesium (mg) | 50 | 6.7 |
| Zinc (mg) | 3.5 | 0.47 |
| Copper (mcg) | 300 | 40.2 |
| Manganese (mcg) | 45 | 6 |
| Iodine (mcg) | 45 | 6 |
| Taurine (mg) | 45 | 6 |
| Vitamin A I.U. | 1500 | 200 |
| Vitamin D I.U. | 300 | 40.2 |
| Vitamin E (mg) | 10 | 1.3 |
| Vitamin K (mcg) | 45 | 6 |
| Vitamin C (mg) | 60 | 8 |
| Vitamin $B_1$ (mcg) | 400 | 53 |
| Vitamin $B_2$ (mcg) | 800 | 127 |
| Vitamin $B_6$ (mcg) | 375 | 50 |
| Vitamin $B_{12}$ (mcg) | 1.15 | 0.2 |
| Niacin (mg) | 6 | 0.8 |
| Panthothenic acid (mg) | 3 | 0.4 |
| Folic acid (mcg) | 67 | 9 |
| Biotin (mcg) | 14.3 | 1.9 |
| Choline (mg) | 37.5 | 5 |
| Inositol (mg) | 22.5 | 3 |
| Moisture % | 3 | |

The level of fat and the exact composition can be controlled in order to yield infant formulas designed to mimic the different lactation periods.

Table 5 shows the fatty acid composition of Fat blend 12 comprising a fat bast of the invention blended with other oils and this used to create a fat source used in an infant formula for use in the invention.

TABLE 5

| Fatty acid | % from total Fatty acids |
|---|---|
| C8:0 | 1.6 |
| C10:0 | 1.5 |
| C12:0 | 10.6 |
| C14:0 | 3.9 |
| C16:0 | 17.2 |
| C16:0 at sn-2 of total fatty acids at sn-2 | 26.3 |
| Ratio (%) of sn-2 palmitic acid of total palmitic acid | 51 |
| C18:0 | 2.4 |
| C18:1 | 41.1 |
| C18:2 | 18.2 |
| C18:3 | 2.2 |
| % fat base (concentrate) in fat blend | 43 |
| Vegetable Oil | |
| Randomized Coconut oil | 22 |
| Randomized Sunflower | 15 |
| Randomized Rapeseed | 20 |

All numbers represent % (w/w), except the ratio which is defined as %. C16:0 represents the total palmitic acid content C16:0 at the sn-2 represents the % palmitic acid at sn-2 of total sn-2 positioned fatty acids. The ratio means the % of sn-2 palmitic acid of total palmitic acid {(% of sn-2 palatine of total sn-2 positioned fatty acids)/3)/(% total palmitin acid)}×100.

Example 3

Effect of Fat Blend on Gastro-Intestinal (GI) Tolerance and Intestinal Maturity

The effect of fat bases and fat blends of the present invention on GI tolerance and intestinal maturity is examined by a clinical study in animal models, in (i) prematurely born rats (Ito Y et al, Intestinal microcirculatory dysfunction during the development of experimental necrotizing enterocolitis Pediatric Research 2007), and (ii) in neonate rat model (Dvorak B, Epidermal growth factor reduces the development of necrotizing enterocolitis in a neonatal rat model, Am J Physiol Gastrointest Liver Physiol, 2002) which both represent models of preterm infants.

The study includes three groups of animals that receive formulas that differ only in their fat composition, mainly the palmitic acid content. One group is administered standard rat milk substitute (that mimics rat milk), the second group is administered rat milk substitute that contains a palmitic acid fat content of about 8% of total fatty acid, of which about 10% is at sn-2 position of the triglyceride and the third group is administered a rat milk substitute that contains fat blend 1 (see Table 2) which contains a total palmitin acid fat content of about 20% of fatty acid, of which ~50% is at sn-2 position of the triglyceride. The formula is administered to all groups for 3 months and their GI tolerance is examined by detailed known GI tolerance and general health at baseline and during the study approximately every month. Further, the intestinal maturity of the study subjects is examined by histological assays at the end of the study. The animals in the first and third group demonstrate better GI tolerance and intestinal maturity than the second group as determined by statistical analysis of questionnaires and by the histological tests. The animals in the third group demonstrate even better GI tolerance and intestinal maturity than the first group as determined by statistical analysis of questionnaires and by the histological tests.

Example 4

The Effects of a Diet Based on Fat Blend 6 on Intestinal Growth, Development and Maturation in Post Weaning Rats The efficacy of a fat blend (see Table 2) on enhancing intestinal growth, development and maturation was investigated in an animal model study. Animals fed with a diet enriched with a high content of palmitic acid at the sn-2 position (Fat blend 6) were compared to animals fed with parallel diets, which contained either similar concentration of palmitic acid or low concentration of palmitic acid.

Study Design

60 Male Sprague-Dawley rats were obtained from the Harlan Laboratories (Rehovot, Israel) at 21 days of age, immediately after weaning and at body weight of 40-50 g. The rats were randomly assigned to receive one of 3 different diets (see Tables 6 and 7); the diets supplied were different only in their fat content:

1. Diet A: Diet with oil containing 21% palmitic acid, of which 48% are esterified at sn-position (contains Fat blend 6 (see Table 2));
2. Diet B: Diet with oil containing 22% palmitic acid, of which 13% are esterified at sn-position;
3. Diet C: Diet with oil containing 8% palmitic acid, of which 11% are esterified at sn-2 position.

The Study was Performed in Two Phases
1. In the first phase, dietary treatment was administered during one week. Rats were randomly assigned to one of the three groups, each group contained 12 animals.
2. In the second phase, dietary treatment was administered for two weeks. Rats were randomly assigned to one of the three groups, each group contained 8 animals.

Following the $8^{th}$ or $15^{th}$ day of feeding, animals were anesthetized, sacrificed and the small intestine was removed and divided into three segments: duodenum, proximal jejunum and terminal ileum. The small intestine segments were used for gross pathology, morphology and histological assays, which indicate intestinal maturity of the study animals.

Diets

All diets were identical with respect to nutrient content and differed only with respect to the type of oil (Tables 6 and 7).

TABLE 6

Fatty acids composition of supplemented oils (% of total fatty acids)

| Fatty acid (% from total FA) | Fat blend 6 | Preparation control I | Preparation control II |
|---|---|---|---|
| C8 | 0.6 | 0.6 | 1 |
| C10 | 0.7 | 0.6 | 0.9 |
| C12 | 8.1 | 8.2 | 13.2 |
| C14 | 2.9 | 3.3 | 4.6 |
| C16 | 21.6 | 22.6 | 8.2 |
| C16:0 at sn-2 of total fatty acids at sn-2 | 31.3 | 9.1 | 2.8 |
| Ratio (%) of sn-2 palmitic acid of total palmitic acid | 48.3 | 13.4 | 11.4 |
| Palmitic acid at sn-2 of total saturated fatty acid at sn-2 | 66 | 37 | 11 |
| C18 | 2.6 | 3.5 | 2.7 |
| C18:1 | 42.7 | 41.9 | 47.3 |
| C18:2 | 18 | 16.4 | 18.8 |
| C18:3 | 1.8 | 1.7 | 1.9 |
| others | 0.90 | 4.6 | 1.4 |

All numbers represent % (w/w), except the ratio which is defined as %. C16:0 represents the total palmitic acid content C16:0 at the sn-2 represents the % palmitic acid at sn-2 of total sn-2 positioned fatty acids. The ratio means the % of sn-2 palmitic acid of total palmitic acid {(% of sn-2 palmitic of total sn-2 positioned fatty acids)/3}/(% total palmitic acid)}×100. Palmitic acid at sn-2 of total saturated fatty acid at sn-2 represents the % palmitic acid at sn-2 of total sn-2 positioned saturated fatty acids.

TABLE 7

Diet Compositions

| | Diet A | Diet B | Diet C |
|---|---|---|---|
| Protein (% by weight) | 19.1 | 19.1 | 19.1 |
| Carbohydrate (% by weight) | 61.9 | 61.9 | 61.9 |
| Fat (% by weight) | 6.2 | 6.2 | 6.2 |
| Calories (kcal/gr) | 3.8 | 3.8 | 3.8 |
| Fat blend 6 (g/kg) | 60 | | |
| Preparation control I (g/kg) | | 60 | |
| Preparation control II (g/kg) | | | 60 |

Food Consumption

During the feeding period, body weight and non-consumed food were weighed twice weekly. Food intake was calculated and expressed as grams per day. Energy and fat intake were calculated corresponding to the amount of ingested food.

Intestinal Gross Pathology and Morphology Analysis

The small intestine was removed and divided into three segments: duodenum, proximal jejunum and terminal ileum. Each segment was weighed and the weight per cm of bowel length was calculated. The segments were opened; bowel circumference in every segment was measured in three different sites and mean bowel circumference was calculated. Mucosa was scraped off and weighed. Bowel and mucosal weight was expressed as mg/cm bowel length/100 g body weight.

Histological Changes Analysis

Histological sections were prepared from the jejunal and ileal remnants.

The intestine for histology was split on the antimesenteric border and washed with iced saline. Pieces of proximal jejunum immediately distal to Treitz ligament and terminal ileum near the ileo-cecal junction were fixed for 24 hours in 5% formalin, washed with absolute alcohol, and embedded in paraffin Transverse 5 μm sections were prepared in a standardized fashion and were stained with Hematoxylin and Eosin. The villus height and crypt depth was measured using the Image Pro Plus 4 image analysis software (Media Cybernetics, Baltimore, Md., USA) and expressed in μm.

Enterocyte Proliferation

Crypt cell proliferation was assessed using a biotinylated monoclonal anti-BrdU antibody system provided in a kit Conn (Zymed Laboratories, Inc, San Francisco, Calif.). Standard 5-bromodeoxyuridine (5-BrdU) labeling reagent (Cat No. 00-0103, Zymed Laboratories, Inc, San Francisco, Calif.) was injected intraperitoneally at a concentration of 1 ml/100 g body weight 2 hours before sacrifice. Tissue slices (5 μm) were deparaffinized and rehydrated with xylene and graded alcohol. The slides were heated for 10 minutes in citrate buffer, pre-treated with denaturating solution for 20 minutes, and incubated with blocking solution for 10 minutes. The sections were stained with a biotinylated monoclonal anti-BrdU antibody for 60 minutes and were then treated with streptavidin-peroxidase for 10 minutes. BRDU-positive color development was obtained by incubating the sections with DUB mixture for 3-5 minutes. An index of proliferation was determined as the ratio of crypt cells staining positively for BrdU per crypts (Shamir et al., 2005, Digestive Diseases and Sciences, Vol. 50, No. 7 pp. 1239-1244 and Sukhotnik et al., 2008 Dig Dis Sci.; Vol 53(5): 1231-9).

Results

Energy Intake, Food and Fat Intake

Food intake increased significantly during the two week period in all animals, without a statistically significant difference between the experimental groups.

Intestinal Mucosal Parameters

Effects of dietary treatment on intestinal mucosal parameters were different in proximal and distal intestine. The tested intestinal mucosal parameters were bowel circumference, bowel weight and mucosal weight Those parameters indicate the physiological development of the intestinal tissue.

In Proximal Intestine

Figure 1:
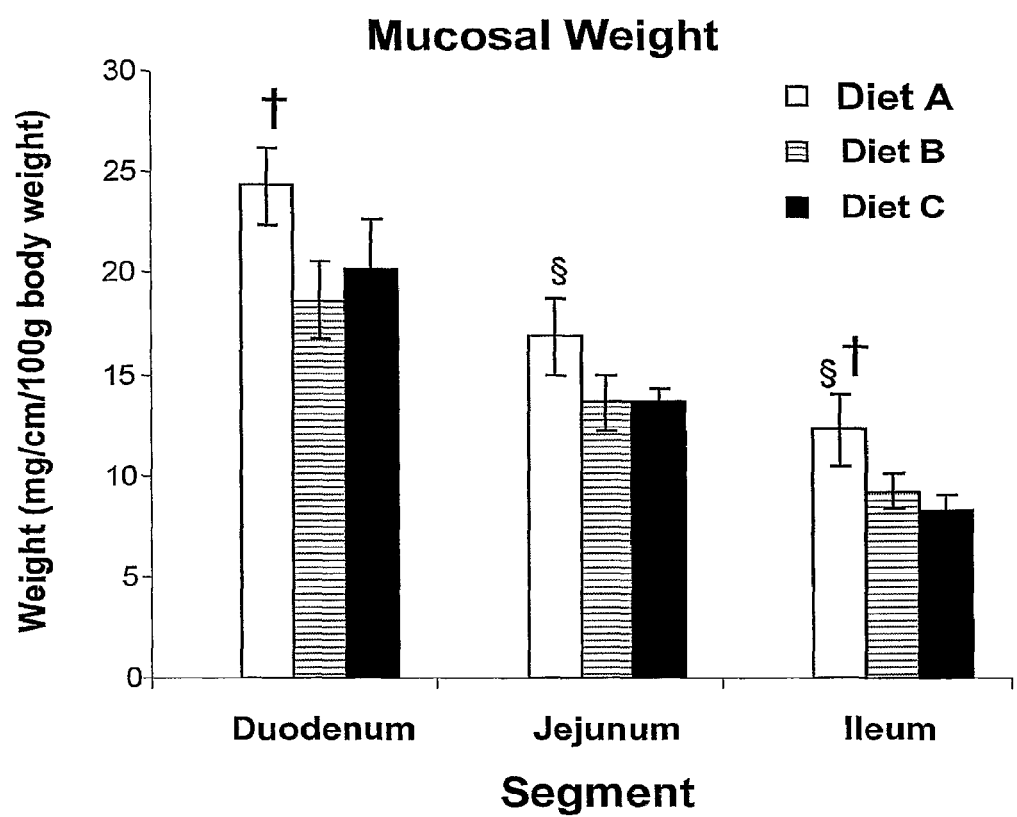
FIG. 1 demonstrates the effect of dietary treatment on mucosal weight of rats after 2 weeks at feeding. Values are mean±SEM. Diet A (containing oils enriched with a high content of palmitic acid at the sn-2 position), Diet B (containing a standard vegetable oil mixture with a high content of palmitic acid) and diet C (containing oils with a low content of palmitic acid) were compared.

In proximal intestine (jejunum and duodenum), following one week of feeding, rats from the diet A group demonstrated statistically significant higher bowel and mucosal weight compared to diet C group (Table 8). It should be emphasized that deprivation of palmitic add in diet C resulted in initial signs of mucosal hypoplasia, which became more prominent after 2 weeks of the dietary treatment After two weeks of feeding, rats from the diet A group demonstrated a trend towards an increase in bowel weight in jejunum when compared to diet B and diet C animals. Mucosal weight of animals fed with diet A was significantly higher compared to diet C animals (p=0.027) (FIG. 1, Table 8).

In Ileum

In ileum, following one week of feeding there were no differences in bowel and mucosal weight between Diet A and Diet B. However rats who received Diet A and Diet B demonstrated greater mucosal weight compared with Diet C animals (Table 8). After two weeks of feeding, diet A exerted a greater bowel and mucosal weight than diet C. Moreover Diet A rats showed higher ileal mucosal weight compared to diet B group (p=0.048) (Table 8).

TABLE 8

Effects of dietary treatment on intestinal mucosal parameters

| Parameters | Diet A | Diet B | Diet C | P value |
|---|---|---|---|---|
| One week feeding | | | | |
| bowel circumference (mm) | | | | |
| Duodenum | 8.0 ± 0.2 | 8.0 ± 0.3 | 8.2 ± 0.1 | |
| Jejunum | 7.3 ± 0.3 | 7.1 ± 0.2 | 7.3 ± 0.3 | |
| Ileum | 6.9 ± 0.2 | 6.3 ± 0.4 | 6.1 ± 0.3 | 0.031 A vs C |
| bowel weight (mg/cm/100 gr BW) | | | | |
| Duodenum | 69.7 ± 3.7 | 63.2 ± 3.5 | 61 ± 3.4 | 0.051 A vs C |
| Jejunum | 54.4 ± 3.6 | 49.1 ± 3.8 | 45.7 ± 2.4 | 0.034 A vs C |
| Ileum | 30.7 ± 2.2 | 32.1 ± 2.4 | 28.7 ± 2.8 | |
| mucosal weight (mg/cm/100 grBW) | | | | |
| Duodenum | 34.7 ± 2.5 | 29 ± 1.7 | 26.7 ± 2.1 | 0.044 A vs B 0.014 A vs C |
| Jejunum | 26.9 ± 3 | 24.2 ± 3.2 | 20.5 ± 1.8 | 0.045 A vs C |
| Ileum | 13.1 ± 0.6 | 13.4 ± 1.6 | 10.2 ± 1.3 | 0.029 A vs C 0.044 B vs C |
| Two week feeding | | | | |
| bowel circumference (mm) | | | | |
| Duodenum | 8.0 ± 0.2 | 8.6 ± 0.1 | 8.3 ± 0.2 | 0.028 A vs B |
| Jejunum | 8.1 ± 0.2 | 7.8 ± 0.2 | 7.4 ± 0.1 | 0.007 A vs C |
| Ileum | 7.6 ± 0.2 | 8.0 ± 0.2 | 6.7 ± 0.4 | 0.051 B vs C 0.054 A vs B |
| bowel weight (mg/cm/100 gr BW) | | | | |
| Duodenum | 53.5 ± 1.9 | 47.8 ± 2.3 | 48.9 ± 2.4 | 0.038 A vs B |
| Jejunum | 38.3 ± 2.2 | 35.9 ± 1.5 | 34.7 ± 1.2 | |
| Ileum | 29.0 ± 1.9 | 26.7 ± 1.9 | 24.5 ± 1.3 | 0.037 A vs C |
| mucosal weight (mg/cm/100 gr BW) | | | | |
| Duodenum | 24.3 ± 1.9 | 18.6 ± 1.9 | 20.2 ± 2.5 | 0.026 A vs B |
| Jejunum | 16.9 ± 1.9 | 13.6 ± 1.4 | 13.6 ± 0.7 | 0.063 A vs C |
| Ileum | 12.3 ± 1.7 | 9.2 ± 0.9 | 8.2 ± 0.9 | 0.027 A vs C 0.048 A vs B |

FIG. 1 shows that Diet A bad an overall improved effect on mucosal weight after two weeks of dietary treatment compared to Diets B and C. Bowel and mucosal weight was expressed as mg/cm bowel length/100 gr body weight (BW)

Microscopic Changes

After one week, feeding diet C resulted in significant shortening of ileal villi compared with the other groups (Table 9). Those effects were enhanced following two weeks of feeding; diet A resulted in significantly greater microscopic changes compared with diet B and diet C (FIG. 2, Table 9). Animals fed with diet A demonstrated taller villi in jejunum (P=0.028) and ileum (P=3.018) compared with diet B animals as well as taller villi in ileum compared with diet C animals (P=0033). Diet A animals also demonstrated significantly deeper crypts in jejunum compared with diet B and C (P=0.015, 0.0016 respectively) and ileum compared with diet B and C (P=0.024, 0.04 respectively). In addition, there was a clear correlation between the histological and the microscopic parameters measurements.

TABLE 9

Effects of dietary treatment on microscopic changes

| Microscopic changes | Diet A | Diet B | Diet C | P value |
|---|---|---|---|---|
| One week feeding | | | | |
| Villus height (μm) | | | | |
| Jejunum | 475.6 ± 27 | 514.6 ± 26 | 447 ± 27.4 | 0.048 B vs C |
| Ileum | 336.9 ± 36 | 281 ± 11.4 | 250.1 ± 10 | 0.015 A vs C 0.041 B vs C |
| Crypth depth (μm) | | | | |
| Jejunum | 199.3 ± 9.7 | 219.7 ± 15 | 194.9 ± 10 | |
| Ileum | 158.6 ± 12 | 173.2 ± 11 | 154.3 ± 11 | |
| Two week feeding | | | | |
| Villus height (μm) | | | | |
| Jejunum | 502 ± 20 | 446 ± 29 | 497 ± 34.5 | 0.028 A vs B |
| Ileum | 298 ± 24 | 230 ± 13 | 231.8 ± 23 | 0.018 A vs B 0.033 A vs C |
| Crypth depth (μm) | | | | |
| Jejunum | 252 ± 10 | 197 ± 7 | 206 ± 9 | 0.0015 A vs B 0.0016 A vs C |
| Ileum | 179 ± 14 | 144 ± 7 | 147 ± 10 | 0.024 A vs B 0.04 A vs C |

FIG. 2 shows that Diet A had an overall improved effect on microscopic bowel appearance after two weeks of dietary treatment compared to Diets B and C.

Enterocyte Proliferation

In Jejunum,

Following one week of feeding animals with diet A resulted in a significant increase in cell proliferation when compared to feeding animals with diet B and C, and feeding animals with diet B increased cell proliferation when compared to feeding rats with diet C. Following two weeks of feeding only diet A rats showed a significantly greater proliferation index in jejunum when compared to diet C rats (P=0.036) (FIG. 3, Table 10).

In Ileum

Following one week of feeding: diet A group exerted a strong stimulation of enterocyte proliferation when compared to diet C group (Table 10).

Following two weeks offending, diet A group exerted a strong stimulation of enterocyte proliferation in ileum. Animals fed with diet A showed a significantly greater proliferation index in ileum when compare to diet B and diet C animals (P=0.0004, 0.0001 respectively) (FIG. 3, Table 10). It should be noted that exposure to diet C resulted in the lowest enterocyte proliferation rates in ileum when compared to other groups (Table 10).

TABLE 10

Effect of dietary treatment on enterocyte proliferation

| enterocyte proliferation (BrdU Positive Cells/10 crypts) | Diet A | Diet B | Diet C | P values |
|---|---|---|---|---|
| One week feeding | | | | |
| Jejunum | 176 ± 3.6 | 167 ± 3.2 | 159 ± 2.4 | 0.042 A vs B<br>0.0011 A vs C<br>0.041 B vs C |
| Ileum | 151.1 ± 5.7 | 140.3 ± 3.7 | 134.3 ± 4.8 | 0.02 A vs C |
| Two week feeding | | | | |
| Jejunum | 171.4 ± 4.4 | 164.3 ± 4.3 | 162 ± 3.4 | 0.036 A vs C |
| Ileum | 170.3 ± 4.5 | 148.5 ± 2.7 | 132 ± 3.8 | 0.0004 A vs B<br>0.0001 A vs C<br>0.0017 B vs C |

Thus, treatment with Diet A resulted in enhanced intestinal development and maturation, detected after the first week of dietary treatment and became more significant after two weeks of treatment. A marked increase in villus height is considered an important index of increased absorptive surface area in this group of animals. Increase in crypt cells along with hypertrophy of the individual cells, which was demonstrated morphometrically, is characteristic of tissues undergoing increased cell proliferation and/or repair.

Deprivation of palmitic acid in diet C resulted in hypoplastic changes in jejunum and especially in ileum. These changes appeared after one week of dietary treatment and increased after 2 weeks of dietary treatment, and they emphasized the detrimental effect of deprivation of palmitic acid. In addition, decrease in enterocyte proliferation was shown in rats fed with low palmitic diet can be considered a major mechanism, responsible for decreasing intestinal cell mass and mucosal hypoplasia.

The dynamic process of intestinal cell turnover is a function of crypt cell proliferation rates, migration along the crypt-villus axis, enterocyte differentiation, and cell death via apoptosis. A significant increase in cell proliferation following Diet A administration was accompanied by a trend toward increase in cell apoptosis, suggesting accelerated cell turnover during intestinal growth.

In conclusion, a high amount of palmitic acid of which a high amount is conjugated at the sn-2 position is an important factor in intestinal growth in post-weaning rats. Diet A resulted in prominent enhanced intestinal development, growth and maturation compared with diets containing a mix of standard vegetable oil mixed with compositions with a high content of palmitic acid or low content of palmitic acid. The prominent enhanced intestinal development, growth and maturation appeared after 1 week and was enhanced alter 2 weeks of dietary treatment Diet A further exerted greater stimulating effects on enterocyte proliferation and turnover compared to the other diets.

The reduction of calcium soap formation is a highly recognized and known beneficial effect of both oils enriched with palmitic acid esterified at sn-2 position and oils with low palmitic acid content (Koo et al., 2006, Journal of American college of Nutrition, Vol 25, No 2 pp 117-122). This effect is similar between these oils and is known to attribute to reducing discomforts and symptoms related to food digestion.

Since Diet A (in the examples above) demonstrated superior and significantly different effects on intestinal development and maturation as compared to Diet C, it is evident that these effects of enhanced intestinal development and maturation are not related to, nor associated with the effect of reducing calcium soap formation.

Example 5

The Effect of Fat Blend on Proliferation and Differentiation of Caco-2 Cells

The effect of a fat blend on proliferation and differentiation in tissue culture was examined in Caco-2 cells. The Caco-2 cell line has been used to date in many qualitative and quantitative studies as an in vitro intestinal epithelial cell model. The cells are grown on permeable inserts from tight-junctions and attain many of the morphological and functional characteristics of small intestinal enterocytes (Artursson P., Karlsson J., 1991, Biochem. Biophys. Res. Commun., Vol 175, 880-885). This cellular model system demonstrated the positive effect of a fat supplement of the invention on intestinal maturation, through cell proliferation and paracellular permeability.

Study Design

Caco-2 cells, originating from a human colorectal carcinoma, were provided by the ATCC (American Type Culture Collection, ATCC® Number HTB-37).

Cells were propagated in Caco-2 Growth Medium under sterile conditions. The cells were subcultured twice prior to treatment. The cell cultures were incubated at 37±1° C., 5±0.5% $CO_2$ and 95±5% humidity, in plastic flasks (NUNC). Caco-2 cellular differentiation and maturation were assessed by cells confluence and paracellular transport.

Confluence and Paracellular Transport

Confluence and paracellular transport were measured in Caco-2 cells seeded on polyester membrane inserts. Confluence and differentiation of the cell monolayer on membrane inserts were measured 7 and 9 days post seeding by the evaluation of the Trans-Epithelial-Electrical-Resistance (TEER) measurements. TEER measurements have become universally established as the most convenient, reliable and non-destructive method for evaluating and monitoring the growth of epithelial tissue cultures in vitro. The confluence of the cellular monolayer, which is a model for intestinal maturity, is determined by an increase in TEER. TEER was measured using the Millicell-ERS (Millipore) electrode during cell incubation in growth medium containing 2 μM of the tested items:

(i) Oil supplement containing low palmitin acid content (8% of total fatty acids with about 10% of which at sn-2 position) (LPO—see Table 11).

(ii) Fat blend 7 containing high palmitin acid content (20% of total fatty acids of which about 50% at sn-2 position) (see Table 2).

TABLE 11

Fatty acids composition of a supplemented oil and a fat blend (% of total fatty acids) before final assay concentrations dilution

| fatty acid (as % from total Fatty acid) | high palmitic acid enriched at sn-2 content oil (Fat blend 7) | low palmitic acid content oil |
|---|---|---|
| C8 | 0.6 | 1.1 |
| C10 | 0.6 | 1.0 |
| C12 | 8.7 | 14.05 |
| C14 | 3.5 | 4.9 |
| C16 | 21 | 8.3 |
| C16:0 at sn-2 of total fatty acids at sn-2 | 31.8 | 2.9 |
| Ratio (%) of sn-2 palmitic acid of total palmitic acid | 50.5 | 11.9 |
| C16:1 | 0.00 | 0.1 |
| C18 | 2.6 | 2.6 |
| C18:1 | 44.4 | 47.6 |
| C18:2 | 16.4 | 18.1 |
| C18:3 | 1.5 | 1.6 |
| C20 | 0.2 | 0.3 |
| C20:1 | 0.3 | 0.4 |

All numbers represent % (w/w), except the ratio which is defined as %. C16:0 represents the total palmitin acid content C16:0 at the sn-2 represents the % palmitin acid at sn-2 of total sn-2 positioned fatty acids. The ratio means the % of sn-2 palmitin acid of total palmitin acid {(% of sn-2 palmitin of total sn-2 positioned fatty acids)/3)/(% total palmitic acid)}×100.

Results

Confluence Parameters

Seven days post seeding, the Caco-2 cell's TEER value in the presence of LPO oil, was 233±59 ohms/cm$^2$. Following an additional two days i.e. 9 days post seeding the Caco-2 cell's TEER value increased by 119.4 (FIG. 4B) and reached 352.5±37 ohms/cm$^2$ (FIG. 4A). In the presence of Fat blend 7, seven days post seeding Caco-2 cells TEER value was 330±11 ohms/cm$^2$ and following additional two days 389±26 ohms/cm$^2$ (FIG. 4A), i.e. increased by 59.2 (FIG. 4B) ohms/cm$^2$. TEER measurement of the control cells showed 325±12 ohms/cm$^2$ and 432±11, 7 and 9 days post seeding correspondingly (FIG. 4A); a total increase of 107.2 ohms/cm$^2$ i.e. more than in the presence of Fat blend 7 (FIG. 4B). As the layer growth rate saturates approached full monolayer, the changes in the LPO oil, being the highest, indicated them to be the least differentiated of the three oils.

Conclusion: the in vitro model showed that Fat blend 7 incubation does not interfere with Caco-2 cells proliferation and differentiation, contrary to incubation with an oil with a low content of palmitic acid. The results indicate that Fat blend 7 promotes intestinal development and faster maturity, while an oil with a low palmitic acid content interferes with intestinal development.

Example 6

The Effect of Palmitic Acid Content in a Diet on the Recovery and Treatment of Short Bowel Syndrome in an Animal Model The effect of diets with different palmitic acid content on prevention and treatment of short bowel syndrome as well as improving intestinal maturation and adaptation is investigated in an animal model study.

Study Design

Animals after either a bowel transection with re-anastomosis or partly small bowel resection are randomly assigned to one of the diet groups that differ only in their palmitic acid content. Following a feeding period, animals are sacrificed and the histological parameters of intestine and the proliferation and apoptosis of enterocytes are studied.

The Study is Performed in Two Phases:
1. In the first phase, dietary treatment is administered d after the induction of short bowel syndrome and the effect of the different diets on recovery from the syndrome is monitored.
2. In the second phase, dietary treatment is administered after the induction of short bowel syndrome and the effect of the different diets to improve the intestinal adaptation recovering from the syndrome is monitored.

Diets

All diets are identical with respect to nutrient content and differ only in palmitic acid content:
1. Diet I: Diet with oil with at least 15% palmitic acid, of which at least 33% are esterified at sn-2 position.
2. Diet II: Diet with oil with at least 15% palmitic acid of which approximately 10% are esterified at sn-2 position
3. Diet III: Diet with oil with approximately 8% palmitic acid of which approximately 10% are esterified at sn-2 position Operation Animals are anesthetized and operated; the abdomen is opened by midline incision. In animals that undergo a partly small bowel resection, a 75% resection is performed, preserving the vascular arcade and leaving 5 cm of proximal jejunum and 10 cm of distal ileum. Intestinal continuity is restored by an end-to-end single layer anastomosis. In animals that undergo bowel transection with re-anastomosis, the intestine is divided and re-anastomosed without resection. Following laparotomy, all animals have access to water for the first 24 h following operation (Sukhotnik at al., 2004, Pediatr Surg Int Vol 20 (4): 235-239).

Food Consumption

During the feeding period, before and after operation, body weight and non-consumed food are weighed Food intake is calculated and expressed as grams per day. Energy and fat intake are calculated corresponding to the amount of ingested food.

The study demonstrates that early exposure of an animal to Diet I results in improving the recovery from short bowel syndrome. Further, exposure of animals after short bowel syndrome induction to Diet I results in increase in overall intestinal wall and mucosal weights and in better recovery rates from short bowel syndrome as shown by the improvement in mucosal adaptation following bowel resection/induction. Animals receiving Diet I have greater mucosal hyperplasia responses in the remaining gut and greater stimulating effects on intestinal re-growth compared to animals receiving other diets.

Example 7

The Effect of Palmitic Acid Content in a Diet on the Prevention and Treatment of Necrotizing Enterocolitis (NEC) in an Animal Model The effect of diets with different palmate acid content on prevention and treatment of necrotizing enterocolitis (NEC) is investigated in a bin-hypothermia-formula-fed preterm animal model study.

Study Design

Animals are randomly assigned to one of the diet groups that differ only in their palmitic acid content.

The Study is Performed in Two Phases:

1. In the that phase, after a feeding period animals undergo NEC induction by hypoxia-hypothermia method the effect of the different diets on incidence and severity of NEC and the survival rare is monitored.
2. In the second phase, dietary treatment is administered after the induction of NEC and the effect of the different diets to improve the intestine recovering is monitored.

NEC Induction Procedure

Experimental NEC is developed by the following procedure; new born pups, starting from 2 hr of age and then every 12 hr, are challenged with hypoxia by breathing 100% nitrogen gas in a closed, clear plastic chamber for 60 see, followed by hypothermia, exposure to cold at 4° C. for 10 min.

Diets

All diets are identical with respect to nutrient content and differ only in palatine acid content.

1. Diet I: Diet with oil with at least 15% palatine acid, of which at least 33% are esterified at sn-2 position.
2. Diet II: Diet with oil with at least 15% palmitic acid of which approximately 10% are esterified at sn-2 position
3. Diet III: Diet with oil with approximately 8% palmitic acid of which approximately 10% are esterified at so-2 position Analyses To study the incidence and severity of NEC, the first feeding with the tested diets starts at 24 hr of age. The pups are randomly assigned to one of diet groups that differ only in their palatine acid content. The animals are fed from birth by orogastric gavage. All pups are observed hourly for clinical signs of NEC such as abdominal distension, respiratory distress, and lethargy. 96 hours after birth, or at signs of illness, the pups are euthanized via decapitation (Travadi et al., 2006, Pediatr Res. Vol 60(2): 185-9). Followed euthanized, the animal's intestinal tissue is processed and examined for gross and histological scoring of damage (NEC).

To study the effects of diets on intestine recovery, animals are fed with the different diets after NEC induction. Intestinal epithelial cell migration (restitution) and proliferation, that are key elements in recovery from intestinal injury, are studied.

To investigate the effect of different diets on enterocyte proliferation and migration, bromodeoxyuridine is administered intraperitoneally 18 hours before sacrifice, with intestine subjected to bromodeoxy-uridine immunohistochemistry (Feng J, Besner G E., 2007, J Pediatr Surg. Vol; 42(1): 214-20).

The study demonstrates that early exposure of an animal to Diet I results in reducing the incidence and severity of NEC. Further, exposure of animals developing clinical signs of NEC illness to Diet I, results in prevention of overall intestinal integrity damage or loss of mucosa. Animals receiving Diet I demonstrate less profound pathologic changes of NEC compared to animals receiving other diets.

The ability of high palmitic acid at sn-2 position to protect the intestines from NEC is due, in part, to its ability to preserve enterocyte migration and proliferation.

Example 8

The Effect of Palmitic Acid Content in a Diet on the Prevention and Treatment of Inflammatory Bowel Diseases in an Animal Model The effect of with different palmitic acid content on prevention and treatment of inflammatory bowel diseases, such as Crohn's disease (CD) and ulcerative colitis (UC), is investigated in an animal model study.

Study Design

Animals developing inflammatory bowel diseases by administration of dextran sulfate sodium (DSS) in their drinking water are randomly assigned to one of diet groups that differ only in their palmitic acid content.

The Study is Performed in Two Chases:

1. In the first phase, after dietary treatment period, DSS is added to the animal's drinking water and the effect of the different diets on prevention or reducing incidence or severity of inflammatory bowel diseases is monitored.
2. In the second phase, dietary treatment is administered after administration of DSS in the animal's drinking water and the effect of the different diets to improve the recovering from inflammatory bowel diseases is studied.

Diets

All diets are identical with respect to nutrient content and differ only in palmitic acid content.

1. Diet I: Diet with oil with at least 15% palmitic acid, of which at least 33% are esterified at sn-2 position.
2. Diet II: Diet with oil with at Least 15% palmitic acid of which approximately 10% are esterified at sn-2 position
3. Diet III: Diet with oil with approximately 8% palmitic acid of which approximately 10% are esterified at sn-2 position Inflammatory Bowl Diseases Induction Administration of DSS in the drinking water of rodents is widely used as an experimental model of UC because it results in acute and chronic colitis and shares clinical and histopathological characteristics with human UC. DSS is a sulfated polymer that induces patchy mucosal injury in a dose-dependent manner. It also induces inflammation, initially through a direct toxic effect on epithelial cells, thereby leading to the development of severe colitis (Vicario et al, 2007, J Nutr.; Vol 137(8): 1931-7).

Food Consumption

During the feeding period, body weight and non-consumed food are weighed. Food intake is calculated and expressed as grams per day. Energy and fat intake are calculated corresponding to the amount of ingested food.

Analyses

For the prevention study, animals are randomly assigned to the different diets. After a feeding period each group is randomly divided into two experimental groups, one receives DSS in their drinking water and the other receives only tap water and the incidence and severity of inflammatory bowel disease are monitored, by measuring of production of some of the mediators involved in the intestinal inflammatory response, such as leukotriene B(4) (LTB(4)), tumor necrosis factor alpha (TNFalpha) and nitric oxide (NO) (Camuesco D, 2005, J Nutr. Vol; 135(4):687-94).

For the treatment study, survivors of inflammatory bowel disease are randomly assigned into diet groups and fed with the different diets. Following a treatment period, animals are monitored for clinical findings (body weight loss, bloody diarrhea, reduced physical activity, severe anemia, shortened colonic length, and perianal injury) (Kishimoto S, 2000, Dig Dis Sci. Vol; 45(8):1.608-16).

Animals are sacrificed and intestinal adaptation is evaluated by histopathological findings (pathological lesion score) and analysis of mucosal villus height (VH), crypt depth (CD), total mucosal height, bromodeoxyuridine (BrdU) incorporation, an index of cell proliferation, and full-thickness DNA and protein content as measures of intestinal adaptive growth (Evans M E, 2005, JPEN J Parenter Enteral Nutr. Vol; 29(5):315-20).

The study demonstrates that early exposure of animal to Diet I results in reducing the occurrence of inflammatory bowel diseases. Further, feeding of animals after inflammatory bowel diseases induction to Diet I results first, in decreasing events occurring in the colonic mucosa (breakdown of the epithelial mucosal banter and higher infiltration of neutrophils) and further, in decrease of induction of severe colitis with diarrhea and colonic mucosal lesions. Total positive alteration in of mucosal function and the inflammation is indicated following feeding of the animals with Diet I.

Example 9

The Effect of Palmitic Acid Content on Enemy Intake Associated with Short Bowel Syndrome in an Animal Model The effect of diets with different palmitic acid content on energy absorption, caloric intake and fat malabsorption associated with short bowel syndrome are investigated in an animal model study.

Study Design

Animals after induction of short bowel syndrome by partly small bowel resection are randomly assigned to one of the diet groups that differ only in their palmitic acid content. Followed feeding, the effect of the different diets on fat malabsorption and intestinal uptake is monitored. It is commonly assumed that when the gastrointestinal symptoms are improved, the amount of energy available from the diet is improved.

Operation

Animals are anesthetized and operated; the abdomen is opened by midline incision. In animals that undergo a partly small bowel resection, a 75% resection is performed, preserving the vascular arcade and leaving 5 cm of proximal jejunum and 10 cm of distal ileum. Intestinal continuity is restored by an end-to-end single layer anastomosis. In animals that undergo bowel transection with re-anastomosis, the intestine is divided and re-anastomosed without resection. Following laparotomy, all animals have access to water for the first 24 h following operation (Sukhotnik at al., 2004, Pediatr Surg Int Vol 20 (4): 235-239).

Food Consumption

During the feeding period, before and after operation, body weight and non-consumed food are weighed. Food intake is calculated and expressed as grams per day.

Analyses

Stool energy losses and the sources of energy within the stool are determined.

Following dietary treatment, stool samples are collected, as are food records. Stools are analyzed for gross energy, total nitrogen, fat content, and fatty acid concentration. Total caloric excretion is tested. The energy content per gram of stool samples is measured by ballistic bomb calorimetry (Miller P S, Payne P R. 1959, A ballistic bomb calorimeter. Br. J Nutr; Vol 13:501-8) on a sample of freeze dried stool. (Murphy at al., 1991, Archives of Disease in Childhood; Vol 66: 495-500).

Diets

All diets are identical with respect to nutrient content and differ only in palmitic acid content
1. Diet I: Diet with oil with at least 15% palmitic acid, of which at least 33% are esterified at sn-2 position.
2. Diet II: Diet with oil with at least 15% palmitic acid of which approximately 10% are esterified at sn-2 position
3. Diet III: Diet with oil with approximately 8% palmitic acid of which approximately 10% are esterified at sn-2 position The study demonstrates that Diet I results in improving the continuing fat malabsorption and energy uptake and decrease stool energy extraction in short bowel syndrome.

Further, exposure of animals after short bowel syndrome induction to diet I results in better recovery rates from short bowel syndrome.

Example 10

The Effect of Palmitic Acid Content in a Diet on the Prevention of Alterations in Intestinal Permeability Associated with Inflammatory Bowel Disease; in an Animal Model The effect of diets with different palmitic acid content on prevention of alterations in intestinal permeability associated with inflammatory bowel diseases, such as Crohn's disease (CD) and ulcerative colitis (UC), is investigated in an animal model study.

Study Design

Animals developing inflammatory bowel diseases by administration of dextran sulfate sodium (DSS) in their drinking water are randomly assigned to one of diet groups that differ only in their palmitin acid content Dietary treatment is administered after administration of DSS and the effect of the different diets on intestinal permeability is studied using bacterial lipopolysaccharide (LPS) leakage from the intestine by examining blood levels of LPS after intestinal loading was applied.

Diets

All diets are identical with respect to nutrient content and differ only in palmitic acid content.
1. Diet I: Diet with oil with at least 15% palmitic acid, of which at least 33% are esterified at sn-2 position.
2. Diet II: Diet with oil with at least 15% palmitin acid of which approximately 10% are esterified at sn-2 position
3. Diet III: Diet with oil with approximately 8% palmitin acid of which approximately 10% are esterified at sn-2 position Inflammatory Bowl Diseases Induction Administration of DSS in the drinking water of rodents is widely used as an experimental model of UC because it results in acute and chronic colitis and shares clinical and histopathological characteristics with human UC. DSS is a sulfated polymer that induces patchy mucosal injury in a dose-dependent manner. It also induces inflammation, initially through a direct toxic effect on epithelial cells, thereby leading to the development of severe colitis (Vicario et al, 2007, J Nutr.; Vol 137(8): 1931-7).

Food Consumption

During the feeding period, body weight and non-consumed food are weighed. Food intake is calculated and expressed as grams per day. Energy and fat intake are calculated corresponding to the amount of ingested food.

Analyses

Survivors of inflammatory bowel disease are randomly assigned into diet groups and fed with the different diets.

Following a treatment period, animals are monitored for clinical findings (body weight loss, bloody diarrhea, reduced physical activity, severe anemia, shortened colonic length, and perianal injury) (Kishimoto S, 2000, Dig Dis Sci. Vol; 45(8):1608-16) and intestinal permeability assay is performed.

Intestinal Permeability Assay

To evaluate the effect of the different diets on intestinal permeability, bacterial lipopolysaccharide (LPS; *Escherichia coli* serotype 0111:B4; Sigma-Aldrich) leakage from the intestine by examining blood levels of LPS after intestinal loading is applied. LPS is given to the animals by gavage. Thirty minutes after loading with LPS, the animals are sacrificed, and blood is collected for analysis by endotoxin assay using the limulus ameobocyte lystate (LAL) kit (BioWhittaker, Walkersville, Md.) (Lambert et al., 2003, J Pharmacol Exp Ther. Vol 305(3):880-6).

Feeding animals after inflammatory bowel diseases induction with Diet I results in prevention of increased intestinal permeability. Diet I feeding is causing a decrease in the levels of plasma endotoxin compared with Diet II and Diet III. The results show that the intestine of animals fed with Diet I is capable of restoring decreases in barrier function during recovery from inflammatory bowel disease.

The invention claimed is:

1. A method for treating in a human child, adult, or geriatric human, short bowel syndrome or inflammatory bowel disease, said method comprising:
   administering to the human child, adult, or geriatric human a therapeutically effective amount of a lipid composition which comprises at least one synthetic triglyceride of the following formula I:

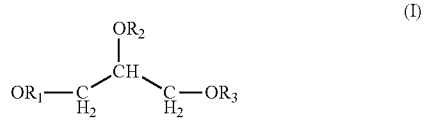

(I)

wherein $R_1$, $R_2$ and $R_3$ may be identical or different and are each independently selected from H or an acyl group with the proviso that at least two of $R_1$, $R_2$ or $R_3$ are acyl groups;
   wherein each of said acyl groups is selected from the group consisting of saturated, mono-unsaturated and poly-unsaturated fatty acid residues with the proviso that $R_2$ is a palmitic acid residue;
   wherein the total palmitic acid residue content is from about 15% to about 55% of the total fatty acid residues in the lipid composition; and
   wherein at least 30% of the total palmitic acid residues are bonded at the sn-2 position of the triglyceride backbone, so as to thereby treat the human child, adult, or geriatric patient.

2. The method of claim 1, wherein at least 13% of the total fatty acids at the sn-2 position of the triglyceride backbone are palmitic acid residues.

3. The method of claim 1, wherein the total palmitic acid residue content is from about 15% to about 40% of the total fatty acid residues in the lipid composition.

4. The method of claim 1, wherein $R_1$ and $R_3$ are unsaturated fatty acid residues.

5. The method of claim 4, wherein at least 50% of the total fatty acid residue at the sn-1 and sn-3 positions of the triglyceride backbone are unsaturated.

6. The method of claim 5, wherein at least 35% of the unsaturated fatty acid residues at the sn-1 and sn-3 positions are oleic acid residues.

7. The method of claim 6, wherein at least 4% of said unsaturated fatty acid residue at the sn-1 and sn-3 positions are linoleic acid residues.

8. The method of claim 7, wherein at least 6% of said unsaturated fatty acid residue at the sn-1 and sn-3 positions are linoleic acid residues.

9. The method of claim 1, wherein the lipid composition consists of:
   0-10% C8:0 fatty acids out of the total fatty acids;
   0-10% C10:0 fatty acids out of the total fatty acids;
   0-22% C12:0 fatty acids out of the total fatty acids;
   0-15% C14:0 fatty acids out of the total fatty acids;
   15-55% C16:0 fatty acids out of the total fatty acids; wherein at least 30% at sn-2 position;
   1-7% C18:0 fatty acids out of the total fatty acids;
   20-75% C18:1 fatty acids out of the total fatty acids;
   2-40% C18:2 fatty acids out of the total fatty acids;
   0-8% C18:3 fatty acids out of the total fatty acids; and other fatty acids are present in levels of less than 8% of the total fatty acids.

10. The method of 1, wherein said lipid composition is prepared from a natural, synthetic or semi-synthetic source.

11. The method of 10, wherein the production of said lipid composition involved an enzymatic catalysis.

12. The method of 1, wherein said composition is a nutritional composition, a pharmaceutical composition, a nutraceutical composition or a functional food.

13. The method of claim 12, wherein said nutritional composition is selected from human milk fat substitute, dairy product, ice-cream, biscuit, soy product, bakery, pastry and bread, sauce, soup, prepared food, frozen food, condiment, confectionary, oils and fat, margarine, spread, filling, cereal, instant product, toddler food, bar, snack, candy and chocolate product.

14. The method of claim 1, comprising administering to said subject said lipid composition in combination with at least one pharmaceutically active agent.

15. The method of claim 1, wherein short bowel syndrome is treated.

16. The method of claim 1, wherein inflammatory bowel syndrome is treated.

* * * * *